United States Patent
Potse et al.

(10) Patent No.: US 6,658,285 B2
(45) Date of Patent: Dec. 2, 2003

(54) CONTINUOUS LOCALIZATION AND GUIDED TREATMENT OF CARDIAC ARRHYTHMIAS

(75) Inventors: Mark Potse, Amsterdam (NL); Andre Linnenbank, Zaandam (NL); Arne Sippens Groenewegen, Burlingame, CA (US); Cornelis Grimbergen, Amsterdam (NL)

(73) Assignee: Resolution Medical, Inc., Pleasanton, CA (US)

( * ) Notice: Subject to any disclaimer, the term of this patent is extended or adjusted under 35 U.S.C. 154(b) by 353 days.

(21) Appl. No.: 09/808,735

(22) Filed: Mar. 14, 2001

(65) Prior Publication Data

US 2002/0038093 A1 Mar. 28, 2002

Related U.S. Application Data

(63) Continuation-in-part of application No. 09/611,179, filed on Jul. 6, 2000.
(60) Provisional application No. 60/200,965, filed on May 1, 2000, provisional application No. 60/189,610, filed on Mar. 15, 2000, and provisional application No. 60/189,611, filed on Mar. 15, 2000.

(51) Int. Cl.[7] .............................................. A61B 5/0402
(52) U.S. Cl. ....................................................... 600/515
(58) Field of Search ................................ 600/515, 518, 600/411, 424; 607/99, 101

(56) References Cited

U.S. PATENT DOCUMENTS

| | | |
|---|---|---|
| 3,565,060 A | 2/1971 | Sipple |
| 4,539,995 A | 9/1985 | Segawa |
| 4,550,502 A | 11/1985 | Grayzel |
| 4,721,114 A | 1/1988 | DuFault et al. |
| 4,751,471 A | 6/1988 | Dunseath, Jr. |
| 4,751,928 A | 6/1988 | Hallon et al. |
| 4,852,572 A | 8/1989 | Nakahashi et al. |

(List continued on next page.)

FOREIGN PATENT DOCUMENTS

| | | |
|---|---|---|
| WO | WO 97/49143 | 12/1997 |
| WO | WO 98/08274 | 2/1998 |
| WO | WO 99/05962 | 2/1999 |

OTHER PUBLICATIONS

Bagliani et al., "Left Origin of the Atrial Esophageal Signal as Recorded in the Pacing Site" *PACE* (1998) 21(1):18–24.

(List continued on next page.)

*Primary Examiner*—Kennedy Schaetzle
(74) *Attorney, Agent, or Firm*—Townsend Townsend & Crew LLP; Mark D. Barrish, Esq.

(57) ABSTRACT

Systems, devices, and methods localize and/or treat arrhythmias of a heart of a patient using signals sensed at an accessible body surface. Based on a database of known heart signals and associated ectopic origin sites or exit sites for treatment guidance, continuous localization identifies candidate ectopic or exit sites throughout a continuous region of tissue. An integral from a selected time interval of a reference heart cycle can be compared statistically with known body surface maps. Statistical interpolation can identify a candidate ectopic or exit site which is different than the known ectopic or exit sites. Relative localization provides accurate site identification from one or more known pacing sites (and the associated heart signals) taken from the patient.

33 Claims, 12 Drawing Sheets

U.S. PATENT DOCUMENTS

| | | | |
|---|---|---|---|
| 4,865,039 A | | 9/1989 | Dunseath, Jr. |
| 4,974,598 A | | 12/1990 | John |
| 5,054,496 A | | 10/1991 | Wen et al. |
| 5,146,926 A | | 9/1992 | Cohen |
| 5,311,873 A | | 5/1994 | Savard et al. |
| 5,313,953 A | | 5/1994 | Yomtov et al. |
| 5,483,968 A | | 1/1996 | Adam et al. |
| 5,609,158 A | | 3/1997 | Chan |
| 5,634,469 A | * | 6/1997 | Bruder et al. ............... 600/512 |
| 5,724,984 A | | 3/1998 | Arnold et al. |
| 5,733,151 A | | 3/1998 | Edsall et al. |
| 5,772,604 A | | 6/1998 | Langberg et al. |
| 5,794,624 A | | 8/1998 | Kwong |
| 5,818,570 A | | 10/1998 | Urbanczyk |
| 5,840,038 A | | 11/1998 | Xue et al. |
| 5,891,049 A | | 4/1999 | Cyrus et al. |
| 5,908,393 A | | 6/1999 | Albrecht et al. |
| 6,038,476 A | | 3/2000 | Schwartz |
| 6,047,206 A | | 4/2000 | Albrecht et al. |
| 6,308,093 B1 | * | 10/2001 | Armoundas et al. ........ 600/509 |

OTHER PUBLICATIONS

Lesh et al., "Comparison of the Retrograde and Transseptal Methods for Ablation of Left Free Wall Accessory Pathways" *Journal of American College of Cardiology*, (1993) 22(2):542–549.

Linnenbank et al., "Choosing the resolution in AD conversion of biomedical signals" *Building Bridges in Electrocardiology*, van Oosterom et al., Eds., Proceedings of the XXIInd International Congress on Electrocardiology, Nijmegen, The Netherlands (Jun. 25–29, 1995) 3 pages total.

Marchlinski et al., "Magnetic Electroanatomical Mapping for Ablation of Focal Atrial Tachycardias" *PACE* (1998) 21:1621–1635.

Metting van Rijn et al., "High–quality recording of bioelectric events, Part 2: low noise, low–power multichannel amplifier design" *Medical & Biological Engineering % Computing* (1991) 29:433–440.

Meeting van Rijn et al., "Patient isolation in multichannel bioelectric recordings by digital transmission through a single optical fiber" *IEEE Transactions on Biomedical Engineering* (1993) 40(3):302–308.

Meeting van Rijn et al., "Amplifiers for bioelectric events: A design with minimal number of parts" *Medical & Biological Engineering & Computing* (1994) 32:305–310.

Meurling et al., "Non–invasive Assessment of Atrial Electrophysiology in AF–Influence of Posture Change" *Computers in Cardiology* (1998) 25:637–640.

Peeters et al., "Clinical application of an integrated 3–phase mapping technique for localization of the site of origin of idiopathic ventricular tachycardia" *Circulation* (1999) 99:1300–1311.

Potse et al., "Continuous localization of cardiac activation sites using a database of multichannel ECG recordings" *IEEE Trans. Biomed. Eng.* (Submission date 2000) 8 pages total.

Potse et al., "Software Design for Analysis of Multichannel Intracardial and Body Surface Electrocardiograms" *Software for Multichannel ECG Analysis* (Draft date 2000) 7 pages total.

Potse et al., "Influence of Chronic Myocardial Infarction on Exit Site Localization of Ventricular Tachycardia Using Paced Body Surface Mapping" *Proceedings of IEEE Trans. Biomed. Eng.* (Draft date 2000) 3 pages total.

Rodefeld et al., "Global Electrophysiological Mapping of The Atrium: computerized three–dimensional mapping system" *Pacing and Clinical Electrophysiology journal* (1997) 20(9):2227–2236.

Sedaaghi, "ECG Wave Detection Using Morphological Filters" *Applied Sig. Process* (1998) 5:182–194.

Seitman, David T., "Body Surface Potential Map Presentations" *Proc of the N. Engl Bioeng Conf, 4th, Yale Univ, New Haven, Conn*, (May 7–8, 1976). pp. 275–278.

SippensGroenewegen et al., "A radiotransparent carbon electrode array for body surface mapping during cardiac catheterization" *Proceedings of the Ninth Annual Conference of the IEEE Engineering in Medicine and Biology Society* (Nov. 13–16, 1987) Boston, MA,, 4 pages total.

SippensGroenewegen et al., "Body Surface Mapping of Ectopic Left and Right Ventricular Activation" *Circulation* 1990) 82(3):879–896.

SippensGroenewegen et al., "Body Surface Mapping of Ectopic Left Ventricular Activation" *Circulation Research* (1992) 71(6):1361–1378.

SippensGroenewegen et al., "Design and Clinical Application of a Body Surface Mapping Reference Data Base for Detailed Localization of Ventricular Tachycardia Foci in Patients Without Structural Cardiac Disease" from Shenasa M, Borggrefe M, and Breithardt G, (eds). *Cardiac Mapping*, Mount Kisco, NY, Futura Publishing Co., Inc., (1993) pp. 347–366.

SippensGroenewegen et al., "Localization of the Site of Origin of Postinfarction Ventricular Tachycardia by Endocardial Pace Mapping" *Circulation* (1993) 88(5):2290–2306.

SippensGroenewegen et al., "Value of body surface mapping in localizing the site of origin of ventricular tachycardia in patients with previous myocardial infarction" *J. Am. Coll. Cardiol.* (1994) 24(7):1709–1724.

SippensGroenewegen et al. "Current Role of On–Line Body Surface Mapping in Postinfarction Ventricular Tachycardia Localization Using Catheter Pace Mapping"; Yasui et al. (Eds.) "Advances in Body Surface Mapping and High Resolution ECG" *Proceedings of Satellite Symposium on Body Surface Mapping and High Resolution Electrocardiography, Yokohama*, (1994) 141–155.

SippensGroenewegen et al., "Body surface mapping during pacing at multiple sites in the human atrium" *Circulation* (1998) 97:369–380.

SippensGroenewegen et al., "Body Surface Mapping of Atrial Arrhythmias" *Journal of Electrocardiology* (Supplement) (1998) 31:85–91.

SippensGroenewegen et al., "Atlas of Paced Body Surface QRS Integral Maps for Localization of the Site of Origin of Postinfarction Ventricular Tachycardia" *Journal of Electrocardiology* vol. 27 Supplement, pp. 105–112.

SippensGroenewegen, A., "Database of Body Surface ECG P Wave Integral Maps for Localization of Leftsided Atrial Arrhythmias" (Draft dated 2000) pp. 1–27.

SippensGroenewegen et al., "Body Surface Mapping of Counterclockwise and Clockwise Typical Atrial Flutter: A Comparative Analysis With Endocardial Activation Sequence Mapping," To be published in *Journal of American College of Cardiology*, (Jun. 2000) pp. 1–35.

Tang et al., "Use of P Wave Configuration during Atrial Tachycardia to Predict Site of Origin" *Journal of American College of Cardiology* (1995) 26(5):1315–1324.

Waktare et al., "Optimal Lead Configuration in the Detection and Subtraction of QRS and T Wave Templates in Atrial Fibrillation" *Computers in Cardiology* (1998) 25:629–632.

Yoshida et al., "A Case of Successful Ablation of Ectopic Atrial Tachycardia whose Origin was Detected by Isopotential Mapping" *Respiration and Circulation* (1998) 46(7):717–721.

Hewlett Packard Product Brochure entitled "EAST™ 12–Lead ECG Monitoring" (1999) 2 pages total.

Lifeshirt.com "Vital signs online" (Mar. 30, 2000) http://www.lifeshirt.com/, 1 page total.

Meridian Medical Technologies, Inc. Internet Wire, "Meridian Announces U.S. Clinical Studies with Innovative Prime ECG™ Mapping System" (Mar. 30, 2000) http://www.internetwire.com/technews/me/me990588.dsl, 2 pages total.

Meridian Medical Technologies, Inc. Internet, "Cardiopulmonary Systems" (Mar. 30, 2000) http://www.meridainmeds.com/cardio.html, 2 pages total.

Meridian Medical Technologies, Inc. Internet, "Prime ECG™ The new standard of care in heart attack detection" (Mar. 30, 2000) http://www.meridianmeds.com/prime.htm, 2 pages total.

* cited by examiner

Site A
⊕ 4.1 mVms
⊖ 2.5 mVms

Site B
⊕ 3.7 mVms
⊖ 2.0 mVms

Site C
⊕ 3.9 mVms
⊖ 1.5 mVms

Site D
⊕ 3.2 mVms
⊖ 1.7 mVms

Site E
⊕ 6.7 mVms
⊖ 3.3 mVms

Site F
⊕ 5.7 mVms
⊖ 2.9 mVms

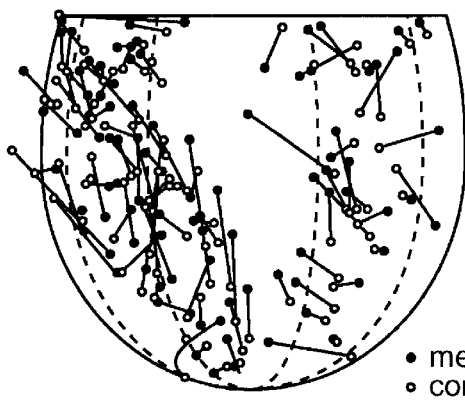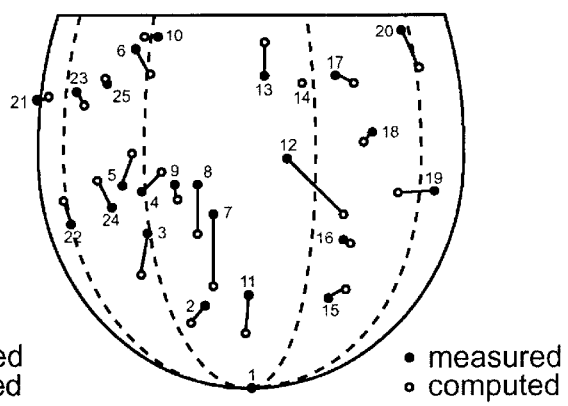
FIG. 13A  FIG. 13B
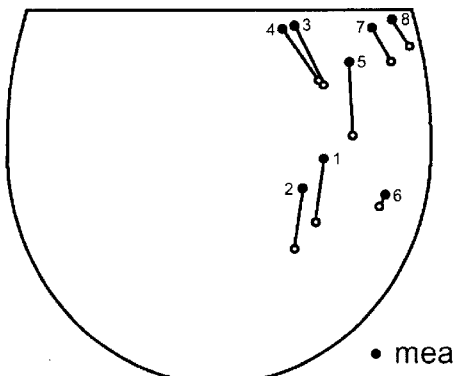
FIG. 14
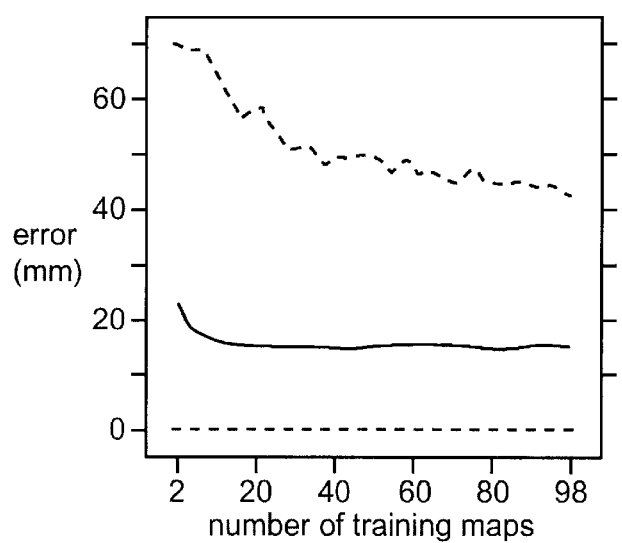
FIG. 15

Skin Side

Top Side

Skin Side

Top Side

CONTINUOUS LOCALIZATION AND GUIDED TREATMENT OF CARDIAC ARRHYTHMIAS

CROSS-REFERENCES TO RELATED APPLICATIONS

This patent application is a continuation-in-part of and claims priority from U.S. patent application Ser. No. 09/611,179 filed Jul. 6, 2000, and also claims priority from U.S. Provisional Patent Application No. 60/200,965 filed May 1, 2000; and U.S. Provisional Patent Application Nos. 60/189,610 and 60/189,611, both filed on Mar. 15, 2000.

The subject matter of this application is related to that of a concurrently filed application entitled: QRST Subtraction Using an Adaptive Template for Analysis of T-Wave Obscured Atrial Activity, U.S. patent application Ser. No. 09/809719; and is also related to that of U.S. patent application Ser. No. 09/724,947 filed Nov. 28, 2000, and U.S. Provisional Patent Application Nos. 60/196,204 filed Apr. 11, 2000, and 60/189,513 filed Mar. 15, 2000. The full disclosures of all of these applications are incorporated herein by reference.

BACKGROUND OF THE INVENTION

I. Field of the Invention

The present invention generally relates to devices, systems, and methods for diagnosing and/or treating the heart. In a particular embodiment, the invention provides techniques for localizing and/or treating arrhythmias.

Significant progress has recently been made toward effective treatments of many cardiac arrhythmias. Contraction of a healthy human heart generally propagates through the heart tissue from the sinus node in the right atrium, and eventually the associated ventricles. This normal propagation of contraction forces blood to flow from the atria to the ventricles in a synchronized pumping action. Arrhythmias of the heart often originate at and/or propagate from alternative heart tissues, resulting in rapid irregular or regular contractions of some or all of the heart. Radiofrequency intracardiac catheter ablation of the alternative ectopic origin, an abnormal contraction pathway, or an abnormal pathway exit site is now used to effectively treat a variety of arrhythmias.

Although quite effective, current catheter ablation for treatment of cardiac arrhythmias has significant disadvantages. A particular challenge in an effective catheter ablation treatment is the time required for proper identification of the treatment site. As it is generally desirable to limit the size of the ablation, significant time is often spent testing candidate ablation sites. The testing often involves pacing, in which an artificial arrhythmia is initiated with a small electrical pulse from a catheter. The candidate sites are often tested sequentially by positioning the intracardiac catheter against a site within (for example) the right ventricle, identifying the engaged tissue location within the ventricle, sensing and/or pacing the heart cycles at the candidate site, repositioning the intracardiac catheter to a new candidate site, and repeating this process until an ectopic origin or an abnormal pathway exit site has been identified.

As fluoroscopy is often used to identify the location of the engaged tissue, this sequential iterative process can result in significant exposure of the patient and treating personnel to potentially harmful radiation. While alternative (and more complex) intracardiac catheter probe structures have been proposed to allow more rapid identification of the ectopic origin(s) of ventricular tachycardias (VTs) and other focal or re-entrant arrhythmias, the size and cost of these complex structures may limit their acceptability.

To overcome the disadvantages associated with the known, time consuming and/or invasive intracardiac arrhythmia sensing and localization techniques, researchers have been working on alternative arrhythmia localization techniques which rely on body surfacing mapping, often during pacing. Electrocardiograms (ECG) may be recorded during abnormal atrial or ventricular activity and compared with ECGs taken during pacing at different sites within the heart to help identify the ectopic or exit site, with the ECGs optionally taken using a standard 12-lead ECG system. More detailed information regarding ectopic or exit sites can be obtained by recording heart cycle signals at the body surface using a more comprehensive sensor array (sometimes called body surface ECG mapping). These heart cycle signals, which generally comprise small amplitude variations in electrical potential along the anterior and/or posterior torso, can be manipulated and/or mapped so as to provide an indication of the origin of the arrhythmia within the heart. Much of this work has concentrated on VT. More recent work has begun to investigate the possibility of localizing certain atrial arrhythmias, such as right atrial tachycardia. U.S. Provisional Patent Application No. 60/189,610, previously incorporated by reference, describes exemplary methods and systems for localization and treatment of atrial fibrillation.

While the new body surface mapping techniques appear quite promising, the previously proposed localization techniques generally have significant limitations. Specifically, many previous techniques involve comparison of ECG morphology or body surface map shape of the patient during an arrhythmia to a series of discrete known maps or plots of heart signals from previous pacing tests. The known map which most nearly matches the map of the patient is selected, and the ectopic or exit site of the patient is then initially assumed to be the same as a known ectopic or exit site associated with the selected known map. Unfortunately, although such methods are quite effective at identifying an arrhythmogenic region within a chamber of a heart, there will often be significant differences between a particular patient's ECG morphology or body surface map (and the associated ectopic or exit site) and the discrete contents of any database.

In light of the above, it would be beneficial to provide improved devices, systems, and methods for localizing and/or treating arrhythmias within a heart of a patient. It would be particularly beneficial to provide methods and systems which could help locate ectopic and exit sites from across a continuous region of tissue, rather than merely selecting a candidate region from a group of discrete results. The present invention provides such improvements, mitigating and/or overcoming at least some of the disadvantages of known approaches for diagnosing and treating arrhythmias.

II. Related Art

The following patents may be relevant to the subject matter of the present invention, and their full disclosures incorporated herein by reference: U.S. Pat. No. 5,311,873; and U.S. Pat. No. 5,634,469. Peeters, H.A.P., SippensGroenewegen, A. and others described "Clinical Application of an Integrated 3-Phase Mapping Technique for Localization of the Site of Origin of Idiopathic Ventricular Tachycardia" in Circulation, 99:1300–1311 (1999). SippensGroenewegen, A. et al. also described "Body Surface Mapping of Atrial Arrhythmias: Atlas of Paced P wave

*Integral Maps to Localize the Focal Origin of Right Atrial Tachycardia*", in *J. Electrocardiol.*, 31(Supp.):85–91 (1998). Related work was described by SippensGroenewegen, A. et al. in, "*Value of Body Surface Mapping in Localizing the Site of Origin of Ventricular Tachycardia in Patients with Previous Myocardial Infarction*", *J. Am. Coll. Cardiol.* 24:1708–1724 (1994). Each of these references is incorporated herein by reference.

SUMMARY OF THE INVENTION

The present invention provides improved systems, devices, and methods for localizing and/or treating arrhythmias of a heart of a patient. Advantageously, the techniques of the present invention generally make use of heart signals sensed on an accessible body surface, generally using an array of heart sensors distributed across a torso of the patient. The invention often makes use of a database of known heart signals and associated ectopic sites or exit sites. Rather than merely selecting a discrete known ectopic or exit site associated with heart signals most nearly matching those of a particular invention, the invention can provide continuous localization to identify candidate ectopic or exit sites throughout a continuous region of tissue.

The known and measured heart signals may be compared by generating integral body surface maps of the patient's torso from a selected time interval of a reference heart cycle. A body surface map for the patient is then statistically compared with the database of known signals. The statistical comparison allows interpolation of a candidate ectopic or exit site which is different than the known ectopic or exit sites from the database. This method is particularly advantageous for relative localization when at least one of the known ectopic or exit sites (and the associated known heart signals) are based on measurements taken from the patient undergoing diagnosis and/or treatment. In other embodiments body surface potentials may be sensed and/or mapped at a single time.

In a first aspect, the invention provides an arrhythmia localization method making use of a database. The database includes known heart signals and associated discrete known ectopic or exit sites. The arrhythmia localization method comprises measuring heart signals during an arrhythmia, and identifying a candidate ectopic or exit site which is different than the known sites by comparing the measured heart signals to a plurality of the known heart signals.

The heart signals may be sensed with an array of sensors distributed across an accessible body surface. The array will often have at least 6 sensing locations distributed across a torso of the patient. Preferably, a selected portion of the measured heart signals from a desired reference heartbeat are integrated at each sensing location to determine an associated integral value. The reference heartbeat may include a premature atrial beat or the initiation of an arrhythmia (particularly for atrial fibrillation), and a data matrix is generated by arranging the integral values according to their associated sensing locations. The data matrix is compared with data matrices of the database generated from the known heart signals. The comparison includes statistical interpolation between a plurality of the known sites to identify the candidate ectopic or exit site. Optionally, correlations between the known heart signals and known sites of the database are determined, facilitating the statistical comparison of the measured heart signals with the known heart signals.

Typically, the database will be normalized by transforming the known sites into a uniform coordinate system. Radial coordinate systems such as a polar coordinate or a cylindrical coordinate system are particularly beneficial, with the exemplary uniform coordinate system comprising a cylindrical coordinate system having an axis extending from an apex of the lower heart chamber to a mitral or tricuspid valve ring, with positioning along the axis often being normalized based on a distance between these two structures. Radial positioning of the axis may be relative to an aortic or pulmonic valve ring. In many embodiments, a position of a chamber of the heart of the patient will be established by identifying datum locations of the chamber, for example, by identifying an apex of a ventricle, a center of a mitral or tricuspid valve, and a center of an aortic or pulmonic valve. This facilitates applying the normalized database from the uniform coordinate system to a particular patient's anatomical geometry.

Paced heart signals will often be measured by initiating an artificial arrhythmia at a pacing site of the patient. The candidate site identification will often be based at least in part on these paced signals. The candidate site will often be determined by calculating an estimated ectopic or exit site using the measured heart signals and the known heart signals. An estimated pacing site may also be calculated from the paced heart signals and the known heart signals. The estimated site can be modified to generate the candidate site based on, for example, a difference between the estimated pacing site and the actual pacing site. In general, the methods and systems of the present invention will benefit from accurate determinations of actual positions within a heart, which may be provided using biplane fluoroscopy, magnetic position sensing, ultrasound position sensing, electrical position sensing, or the like. Initiating a plurality of artificial arrhythmias at a plurality of pacing sites of the patient may allow identification of the candidate site using the pacing data. In fact, the database may be specific for the patient of interest and based entirely on paced data from the patient.

In many embodiments, a heart tissue will be imaged and the candidate site will be graphically indicated on an image of the heart tissue. The image will preferably comprise a three-dimensional image, most often being a biplane fluoroscopic images, and the candidate site will be indicated as a three-dimensional location superimposed on the heart tissue image. This significantly facilitates positioning a catheter at the candidate site by reference to the graphical indication, particularly when an image of the catheter is also visible in the heart tissue display.

In another aspect, the present invention provides an arrhythmia localization system comprising a database having known heart signals and associated discrete known ectopic or exit sites. A heart signal sensor array measures heart signals during an arrhythmia. A processor is coupled to the database and the sensor array. The processor calculates a candidate ectopic or exit site (which is different than the known sites) in response to the measured heart signals and the known heart signals.

Generally, the processor will comprise hardware, software, and/or firmware adapted to perform any or all of the methods of the present invention as described herein. Typically, the processor interpolates between a plurality of the known sites associated with the plurality of known heart signals based on the comparison of the measured heart signals to a plurality of the known heart signals, often using a statistical comparison algorithm. In many embodiments, a catheter (such as an ablation catheter and/or a pacing catheter) will be used with the system, a location of a distal portion of the catheter preferably being transmitted to the processor by a catheter position sensor.

While the invention is useful for absolute localization based on a database built up from many different patients, it is particularly beneficial for relative localization within a particular patient's heart anatomy when the database comprises, at least in part, heart signals and known sites associated with that particular patient.

BRIEF DESCRIPTION OF THE DRAWINGS

FIGS. 13A and 13B graphically illustrate differences between positions of computed ectopic sites compared to actual positions of associated catheter pacing sites, and differences between actual positions of database mean maps and the corresponding computed positions, respectively.

FIG. 14 illustrates computed and measured positions corresponding to eight paced maps obtained at adjacent locations within a single patient.

FIG. 15 graphically illustrates localization error for database mean maps as a function of the number of maps.

DETAILED DESCRIPTION OF THE SPECIFIC EMBODIMENTS

While the following description is largely directed to localization and/or treatment of ventricular tachycardia (VT) and/or atrial fibrillation (AFib), the methods, devices, and systems of the present invention may be used for a wide variety of arrhythmias, including both focal and re-entrant arrhythmias (such as those resulting from infarct scars). When used for treatment of re-entrant arrhythmia, treatment may be directed at or near an exit site of a pathway. The invention may, in some cases, be used with pulmonary vein isolation therapies now being developed (in which linear, circumferential, and/or perimeter lesions may isolate one or more pulmonary veins to inhibit propagation from triggers or exit sites in or near the veins) by allowing selection of target veins and/or indicating whether vein isolation should be utilized. However, the invention is particularly useful for localizing focal arrhythmias and pathways beyond the pulmonary veins, and may find use for treatment of paroxysmal or persistent AFib, atrial tachycardia, arrhythmias of the ventricles, localizing an insertion point of a concealed accessory pathway, and the like.

Figure 1A:
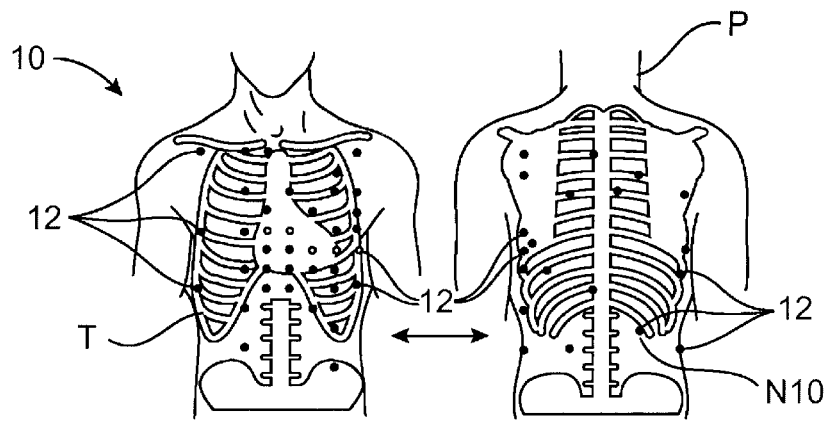
FIG. 1A schematically illustrates a sensor system having an array of sensing locations distributed across a patient's torso.

Referring now to FIG. 1A, the techniques of the present invention will generally make use of an array 10 of sensors 12 distributed across anterior and posterior skin surfaces of torso T on patient P. Array 10 provides multi-lead electrocardiogram (ECG) data at a plurality of sensing locations distributed across torso T, typically at over 20 sensing locations, more preferably at over 40 sensing locations, and ideally at 62 or more sensing locations. Optionally, additional approximated sensor signals may be generated by interpolating between sensors of the array. This may be performed, for example, to generate data at 192 sensing locations when only 62 sensors are present in the array.

Sensors 12 generally comprise unipolar or bipolar electrodes coupled to the patient's skin, or to an alternative accessible tissue surface (for example via a transesophageal approach) suitable for measuring electrical surface potential. Suitable electrode structures may include those described in U.S. Pat. Nos. 5,311,873 and 5,634,496, previously incorporated herein by reference. Exemplary arrays for use in locations having large amounts of electromagnetic noise (such as an electrophysiology lab or other location in which electrosurgery or electrical stimulation of tissues for intracardiac pacing is performed) was described by Metting van Rijn, A. C. et al. in *IEEE Trans. Biomed. Eng.*, BME-40:302–308 (1993). Alternative sensor array structures and associated data acquisition and manipulations components were described by SippensGroenewegen, A. et al. in an article entitled, *"Body Surface Mapping During Pacing at Multiple Sites in the Human Atrium: P wave Morphology of Ectopic Right Atrial Activation"*, Circulation, 97:369–380 (1998); and by Linnenbank, A. C. in a 1996 thesis for the University of Amsterdam entitled, *"On-Site Recording, Analysis, and Presentation of Multi-channel ECG Data"*.

Figure 1C:
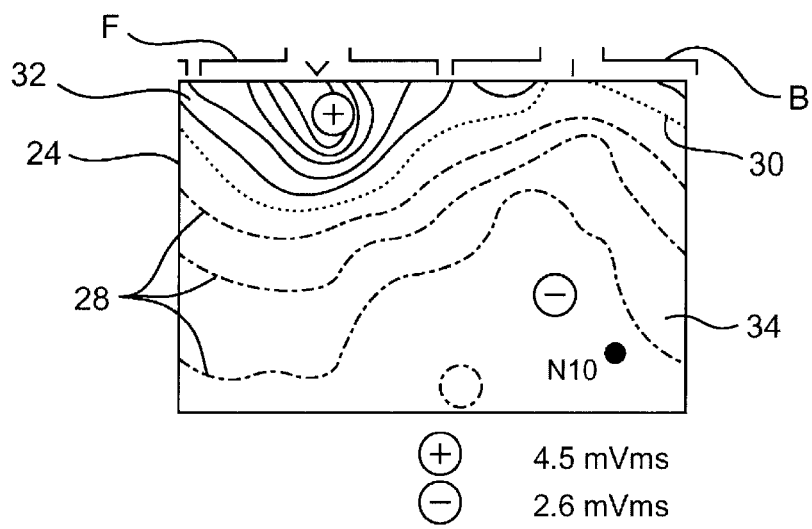
FIG. 1C illustrates a plot of a data matrix generated by mapping the integral values with positions corresponding to the locations of the sensors across the patient's torso.
Figure 1B:
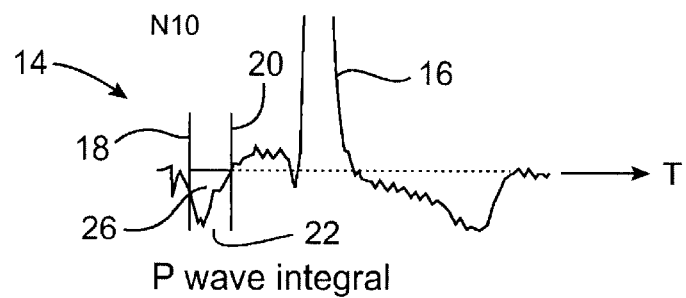
FIG. 1B graphically illustrates the method for calculating an integral value across a selected time portion of a heart signal cycle from a single sensor location.

Referring now to FIG. 1B, electrocardiogram or ECG data is preferably acquired simultaneously from each sensor 12 of array 10 at a sampling rate of over about 500 Hz, ideally at a sampling rate of about 1,000 Hz or more. In some embodiments, sequential sampling of sensor 12 from array 10 may alternatively be used, and higher or lower sampling rates are also feasible. When a lower sampling rate is used, the data may be upsampled using multi-rate filter banks.

Preferably, signals which are absent, for example, due to electrode obscurement by defibrillator patches or lead dislodgment, may be deleted. Poor quality signals may also be visually and/or automatically identified and rejected. Such rejected signals may be replaced using interpolation of adjacent lead recording data. Interpolation techniques may also be utilized to correct for offset variation among electrodes, and for linear baseline drifting.

Graph 14 includes an ECG signal tracing 16 representing the variation in voltage over time, as sensed by sensors 12, optionally at about 1 to 2 ms intervals. Signal tracing 16 may be used to evaluate heart cycle signals from the heart of patient P. In general, one or more reference heart cycles will be selected for manipulation and comparison. The reference heart cycle may be a premature atrial beat or the heart cycle coinciding with initiation of the arrhythmia for AFib, or any cycle during VT, for example. ECG Tracing 16 can be used to determine a beginning 18 and end 20 of a time portion 22 of the reference heart signal cycle which is of particular interest for evaluating one or more regions of the heart. In the example illustrated in FIG. 1B, a P wave onset may be determined by the time at which the voltage progresses beyond 30 $\mu V$ while termination of the P wave may be defined at the atrial J-point, as is generally understood in the field of electrocardiography. Alternative criteria for P wave onset and offset might also be utilized, and automated detection of time portion 22 is also feasible. Alternative time portions may also be selected, for example, QRS data may be analyzed for localization of VT.

Referring to FIGS. 1B and 1C, measurements made at each sensor 12 are preferably mapped onto a data matrix 24 according to the locations of the associated sensor. In the exemplary embodiment, a P wave integral numerical value 24 may be calculated based on heart cycle signals 16 within selected time portion 22 for a particular sensor location N10. This calculated P wave integral value reflects the time/amplitude area of ECG signal at that sensor location within the selected time portion. Similar integral values are calculated for each sensor location, and the sensor values are mapped within data matrix 24 continuously from a portion of the data matrix associated with a front F of torso T, across a side of the patient P, and to a back B portion of torso T. As shown in FIG. 1C, the data matrix will often be presented graphically by calculating lines of constant integral values 28 based on the individual discrete integral values and their associated positions within the data matrix. In some embodiments, this information can be summarized by presenting a single line 30 of zero integral value between a region of positive integral values 32 and a region of negative integral values 34. In much of the description which follows, the region of positive integral values 32 is presented as a shaded region within a graphical depiction of data matrix 24. Exemplary alternative data matrices may be presented with shades of a first color (red, for example) for positive values, a second color (blue, for example) for negative values, and optionally a third color (such as green) for zero.

For localizing of certain arrhythmias, possibly including certain VTs and some types of atrial tachycardia, directly using measurements from sensors 12 to calculate integral values 26 for the selected time portion 22 may be sufficient to identify an arrhythmogenic region (which may be relatively large) of a particular ventricle, and in some cases, a particular atrium. Localizing directly from the sensed heart cycle signals is significantly facilitated when the signals within the time portion of interest are predominantly indicative of activity within a candidate ectopic region of the heart. For example, when localizing VT, selecting a time portion dominated by the QRS complex in the signal can effectively localize arrhythmogenic foci or exit sites, as more fully described in the *J. Am. Coll. Cardiol.*, 24:1708–1724 (1994), the full disclosure of which is incorporated herein by reference. This localizing of tachycardia foci within the ventricle may be facilitated by the domination of the QRS complex in the signal of the overall body surface potential.

Unfortunately, when localizing fibrillation foci within an atrium, the P wave (which can be indicative of activity within the atrium) will often be superimposed, either partially or completely, by the T-U wave. Physiologically speaking, the atrial activity of interest may coincide with ventricular recovery of the preceding cardiac cycle. To accurately localize focal triggers during the initiation of paroxysmal or persistent AFib, the present invention can make use of systems and methods for separating a signal portion of interest from a superimposed signal portion, with the two signal portions often being separated from a single signal sensed from at least one single sensor location. These signal separation techniques are particularly advantageous when used to isolate the P wave from a simultaneously occurring T-U wave. It may be possible in some circumstances to artificially separate these waves by active overdrive pacing using an intracardiac catheter with a pacing period selected to avoid superimposition of these two signal portions during artificially initiated arrhythmia. Alternatively, as will be understood with reference to U.S. Provisional Application No. 60/189,610, a QRST subtraction program can isolate and preserve the P wave morphology so as to enable trigger localization of focal AFib and other arrhythmias. The application of similar subtraction methodologies may also enhance the ability of body surface mapping systems to localize the atrial insertion site of a concealed accessory pathway or to isolate flutter waves with atrial flutter and fibrillation waves with chronic AFib.

Figure 2:
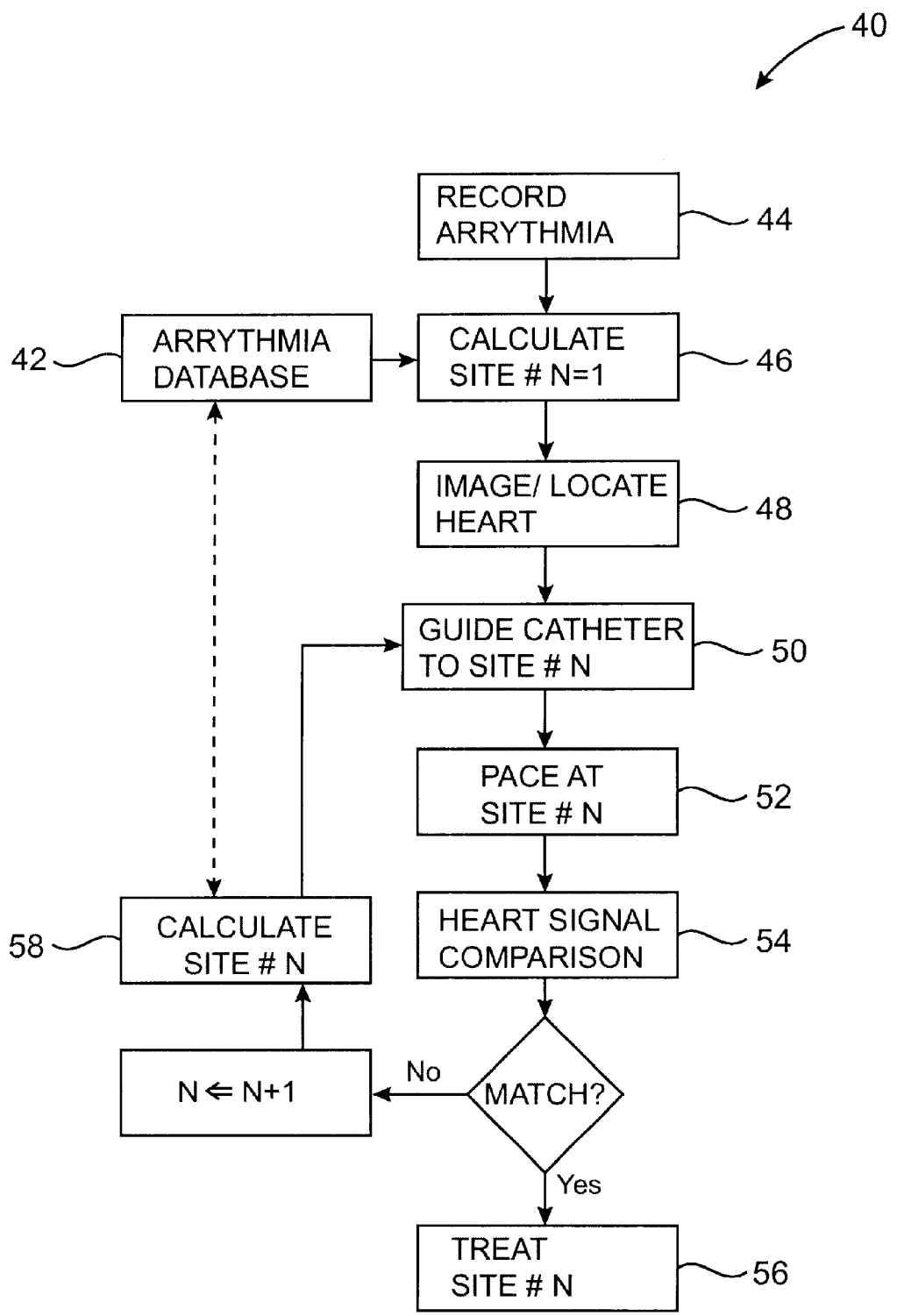
FIG. 2 schematically illustrates a method and computer program for localizing an ectopic or exit site, either absolutely (using a pre-established database) and/or relatively (based at least in part on measurements previously taken from the patient).

Referring now to FIG. 2 an exemplary localization and treatment method 40 will often make use of a pre-existing arrhythmia database 42, the arrhythmia database typically including mean paced maps taken from a variety of individuals at multiple pacing locations, as will be described hereinbelow. When seeking to localize an arrhythmia for a particular patient, heart signals of the arrhythmia for the patient will be captured and recorded 44, preferably using array 10 as described above. The recorded heart signals will often be manipulated as described above to generate one or more integral data matrices and/or plots.

As will be described hereinbelow, statistical comparisons of the recorded arrhythmia 44 to the database 42 will often allow calculation 46 of a candidate ectopic or exit site. The initial calculation may be performed using only surface measurements taken from the patient's body surface and the database of previous patient morphology and associated pacing sites. Use of these external sources of information is generally referred to as "absolute" localization hereinbelow. Alternatively, the methods of the present invention may be used after initiation of pacing, optionally being based entirely on data from the patient.

As described below, it will often be beneficial to accurately identify the location of diagnostic and/or treatment structures (such as a pacing catheter electrode) relative to one or more tissues within the heart, particularly while imaging the heart tissue in three dimensions, for example, using biplane fluoroscopy in an electrophysiology lab. To help establish the location, orientation, and/or dimensions of a heart chamber of interest, anatomical locations in space or datum points may be identified in step 48. In the exemplary embodiment, this information is used to graphically indicate or superimpose the calculated candidate site on the displayed tissue image so as to help guide a diagnosing and/or treatment catheter toward the candidate site 50.

Where further refinement in the localization is desired, the catheter may pace at the candidate site 52 while measurements are taken by sensor array 10 (shown in FIG. 1A). Heart signals measured by the array during pacing may be compared to the heart signals from the original arrhythmia 54. If the paced heart signals match the recorded arrhythmia, the site may be treated 56, using either the same or a different catheter.

If the heart signals obtained by pacing at the candidate site do not match the recorded arrhythmia within a desired tolerance, a new candidate site 58 may be calculated. Optionally, the new candidate site may be calculated by determining an adjustment vector or function. Such specific guiding to one or more sequential pacing sites can significantly decrease the total number of pacing sites required. In some embodiments, this may involve calculating an estimated pacing location from the paced heart signals. The estimated pacing location may be compared to an actual pacing location, which may be determined using a frame grabber and image analysis system coupled to the biplane fluoroscopy to calculate a three dimensional position of a radio-opaque marker (such as an electrode) of the catheter. Alternatively, known magnetic catheter location systems, electrical location systems, ultrasound location systems, or the like might be used. The adjustment vector or offset may then be applied to the calculated candidate site. Optionally, the pacing location and measured heart signals may be added to the database. When sufficient specific information from this patient is available (for example, when three or more pacing locations and associated integral maps have been obtained), the entire database may be specific to the patient undergoing diagnosis or treatment.

As mentioned above, localization which makes use of patient-specific pacing location and heart signal information is sometimes referred to as relative localization. In many embodiments, relative localization will have significant accuracy advantages, particularly when a plurality of pacing locations have been captured. Eventually, when sufficient relative localization accuracy has been achieved, the recorded arrhythmia and paced heart signal will match and treatment can be initiated. Advantageously, the localization system may graphically guide a pacing/ablation catheter to successive candidate sites by superimposing the calculated candidate site with the imaged heart tissue and catheter, ideally in three-dimensions, significantly facilitating the procedure.

Figure 3:
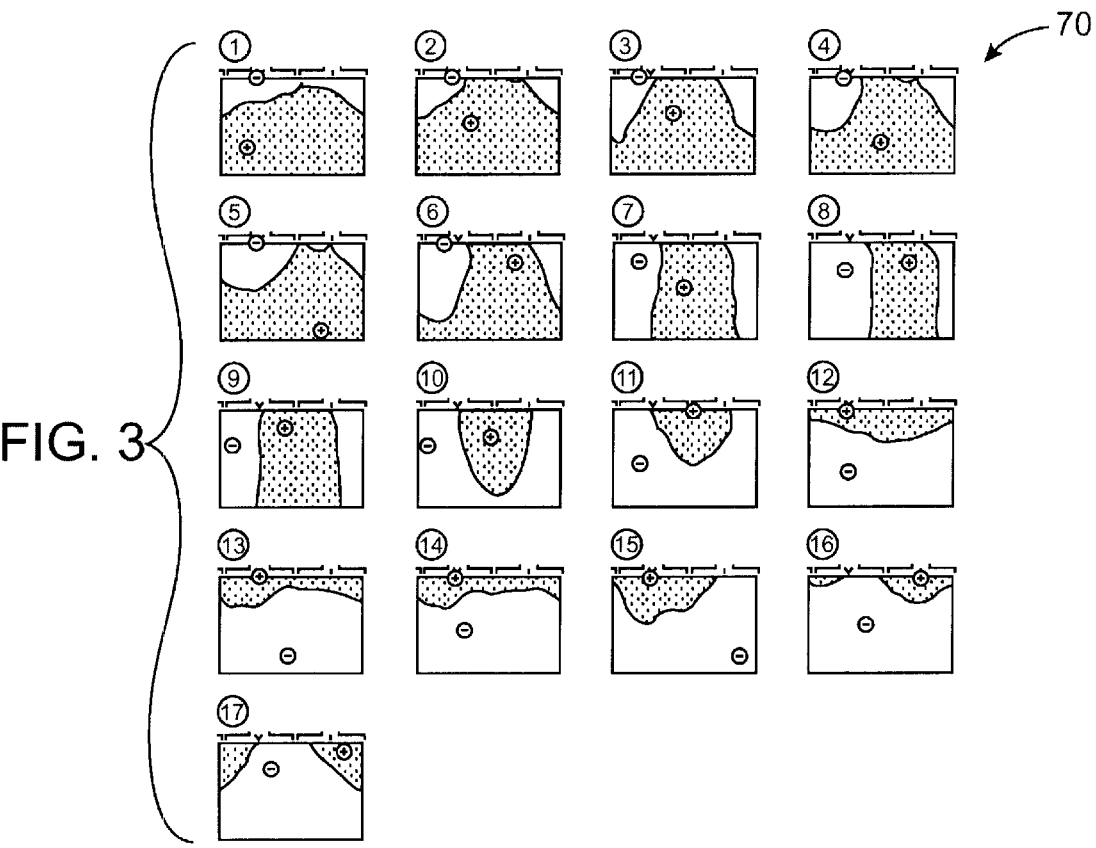
FIG. 3 graphically illustrates a database of known atrial paced heart cycles as 17 mean P wave integral maps.
Figure 4:
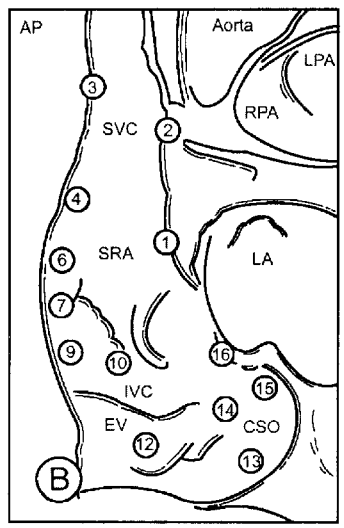
FIGS. 4 and 5 illustrate 17 known right atrial ectopic origins associated with the 17 mean P wave integral maps of FIG. 3.
Figure 5:
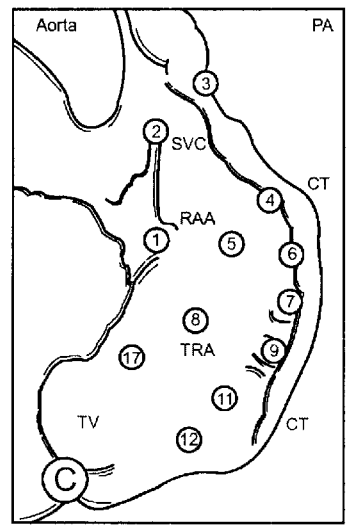
Figure 6A:
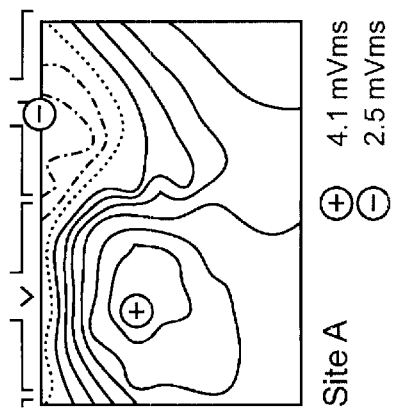
FIGS. 6A–F illustrate correlations between integral maps of paced heart signal cycles obtained in different patients at a common region in the left atrium.
Figure 6B:
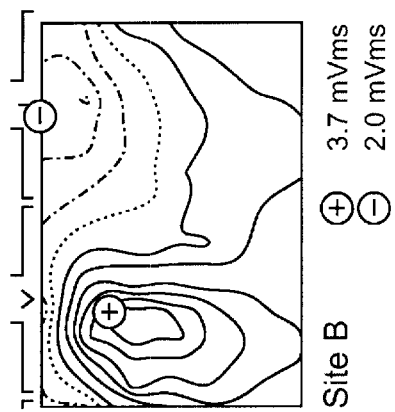
Figure 6C:
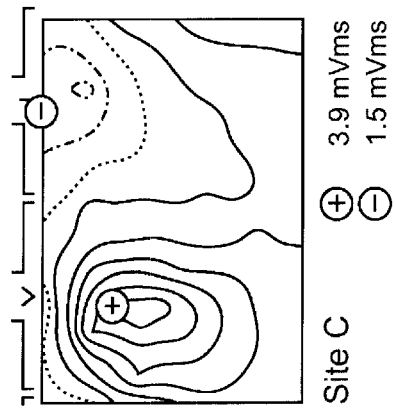
Figure 6D:
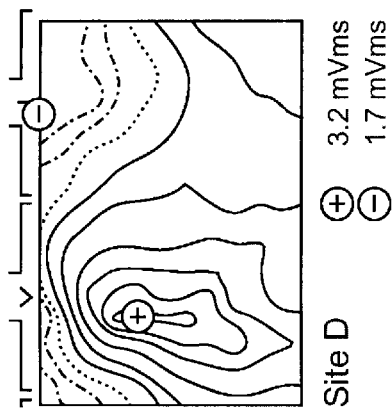
Figure 6E:
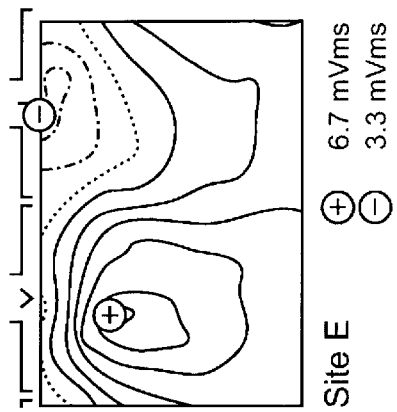
Figure 6F:
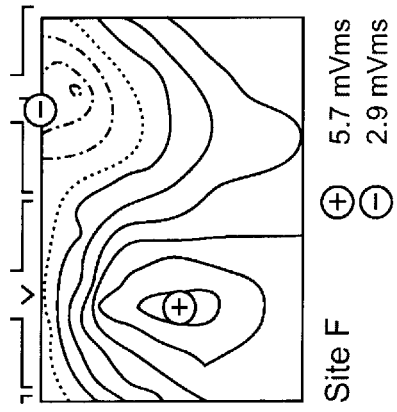

Referring now to FIGS. 3–5, a graphical plot of a particular patient's P wave integral may be used to localize an arrhythmogenic region in an atrium by comparing the P wave integral plot for the patient to a database of P wave integral plots having associated known ectopic foci within the right atrium. Each of the 17 plots of database 70 has an associated ectopic region (identified by the encircled numbers illustrated in FIGS. 4 and 5).

The anterior-posterior AP view shown in FIG. 4 and the posterior-anterior PA view of FIG. 5 illustrate the right atrial cavity. Anatomical landmarks included in these diagrams include the superior vena cava SVC and inferior vena cava IVC; the right atrial appendage RAA; the smooth right atrium SRA; the trabeculated right atrium TRA; the crista terminalis CT; the fossa ovalis FO; the left atrium LA; the Eustachian valve EV; the coronary sinus os CSO; the tricuspid valve TV; the right pulmonary artery RPA; and the left pulmonary artery LPA.

Methods for assembling a right atrial database are described in detail in the *J. Electrocardiol.*, 31–91 (Supp.): 85 (1998), previously incorporated herein by reference. The mean P wave integral maps of atrial database 70 feature extreme positions and zero line contours without positive and negative integral contour lines. Alternative plot formats, such as three-dimensional or chest anatomy-based formats, map displays using various color schemes, and the like, may also be used. A similar left atrial database may be prepared using a trans-septal or retrograde aortic approach, with each database again benefiting from accurate information regarding the positioning of the pacing catheter, as described above and as described in more detail in a U.S. Provisional Application No. 60/196,204 filed on Apr. 11, 2000 and entitled *"Database of Body Surface ECG P Wave Integral Maps for Localization of Left sided Atrial Arrhythmias,"* the full disclosure of which is incorporated herein by reference.

These databases have generally been prepared by grouping together sets of pacing data having similar morphologies and pacing locations from a number of tests. Each of the mean paced maps of the databases and the associated known ectopic or exit sites or regions has been assembled from a series of individual pacing tests on several different patients. Referring now to FIGS. 6A–F, six individual P wave integral maps included within a group were each obtained during pacing at the left upper and left lower pulmonary veins of the left atrium. These six similarly located pacing sites were grouped together within a single group of a left atrial database, and these plots were averaged to produce one of the mean plots of the left atrial database. The spatial or morphological compatibility of these patterns can be clearly seen, particularly with reference to the location and orientations of both the highest positive and negative integral values, as well as with reference to the zero line contour separating the shaded from unshaded regions. While each of these six patient-specific maps were generated using intracardiac pacing, naturally occurring ectopic origins may be identified by comparing reference heart cycle signals measured during premature atrial beats, the onset of AFib, and atrial tachycardia (and optionally separated from superimposed signals as described above) to the mean paced plots of the database.

Figure 7:
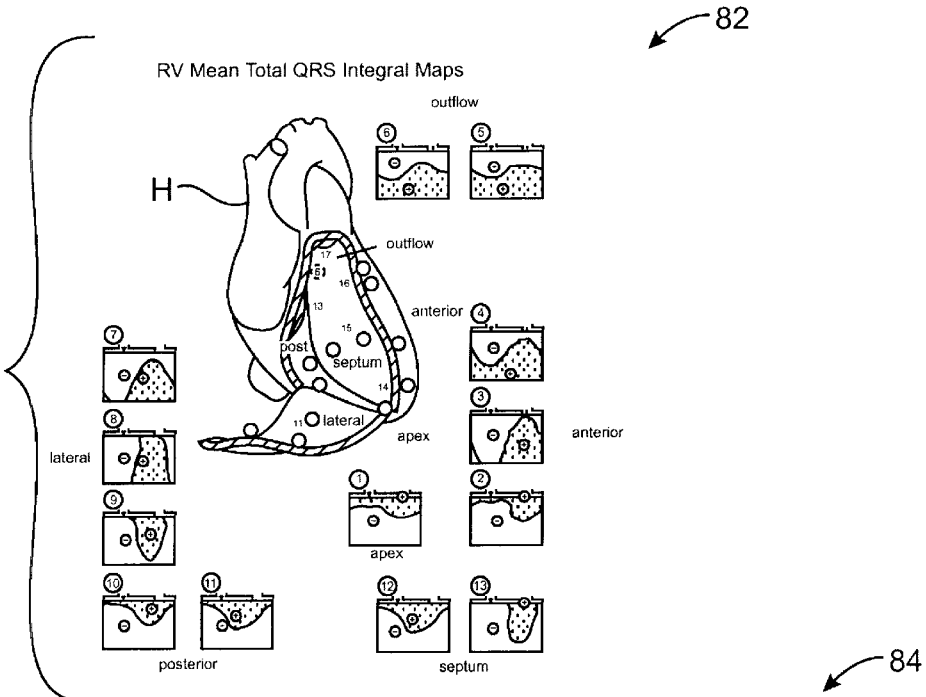
FIG. 7 illustrates a database of QRS integral maps and associated ectopic origins within the right ventricle.
Figure 8:
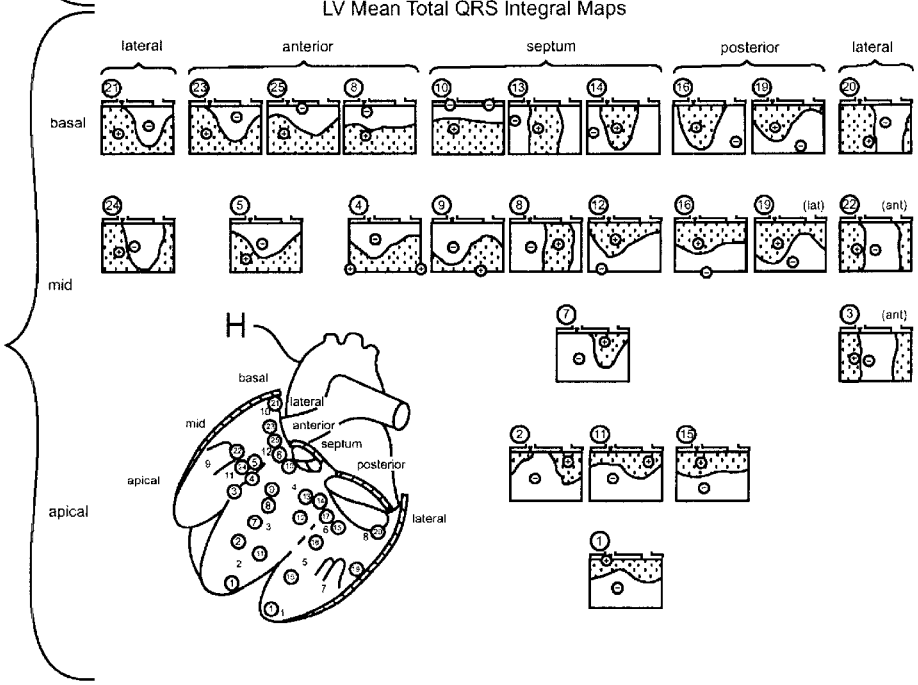
FIG. 8 illustrates a database of QRS integral maps and associated ectopic origins within the left ventricle.

Referring now to FIGS. 7 and 8, a right ventricular database 82 and a left ventricular database 84 each include mean QRS integral maps for paced ectopic origins in the right and left ventricles, respectively. These ventricular databases are more fully described in an article by Peeters, H. A. P. et al. entitled *"Clinical Application of an Integrated 3-Phase Mapping Technique for Localization of the Site of Origin of Idiopathic Ventricular Tachycardia"*, *Circulation* 99:1300–1311 (1999) the disclosure of which is incorporated herein by reference.

Figure 9A:
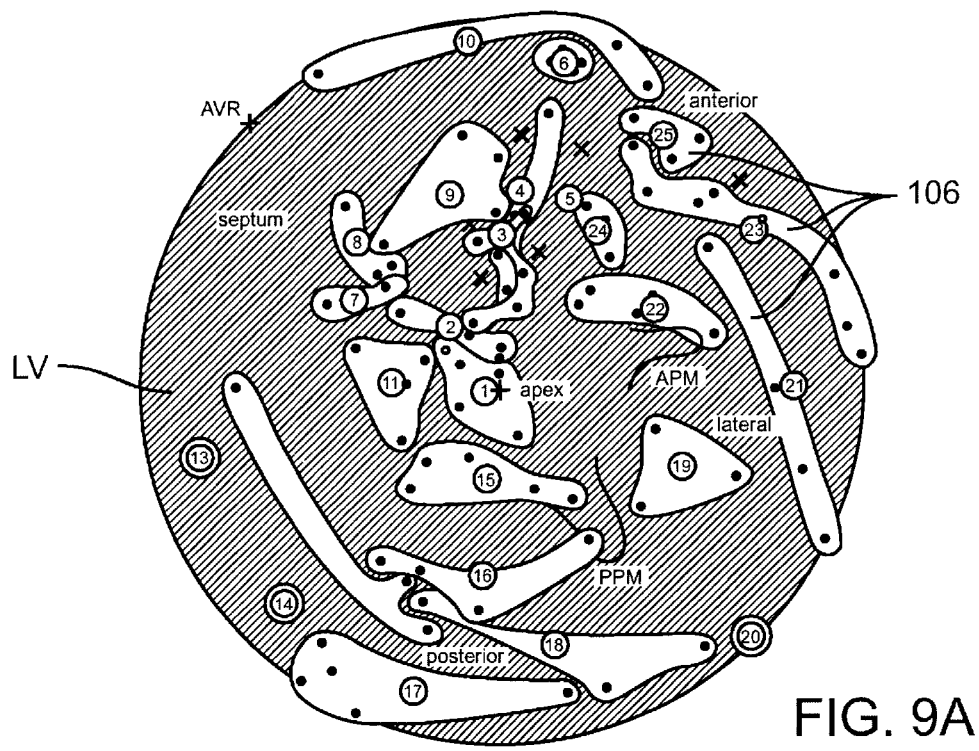
FIGS. 9A and 9B illustrate arrhythmogenic regions of the left and right ventricles, respectively, in polar projection.
Figure 9B:
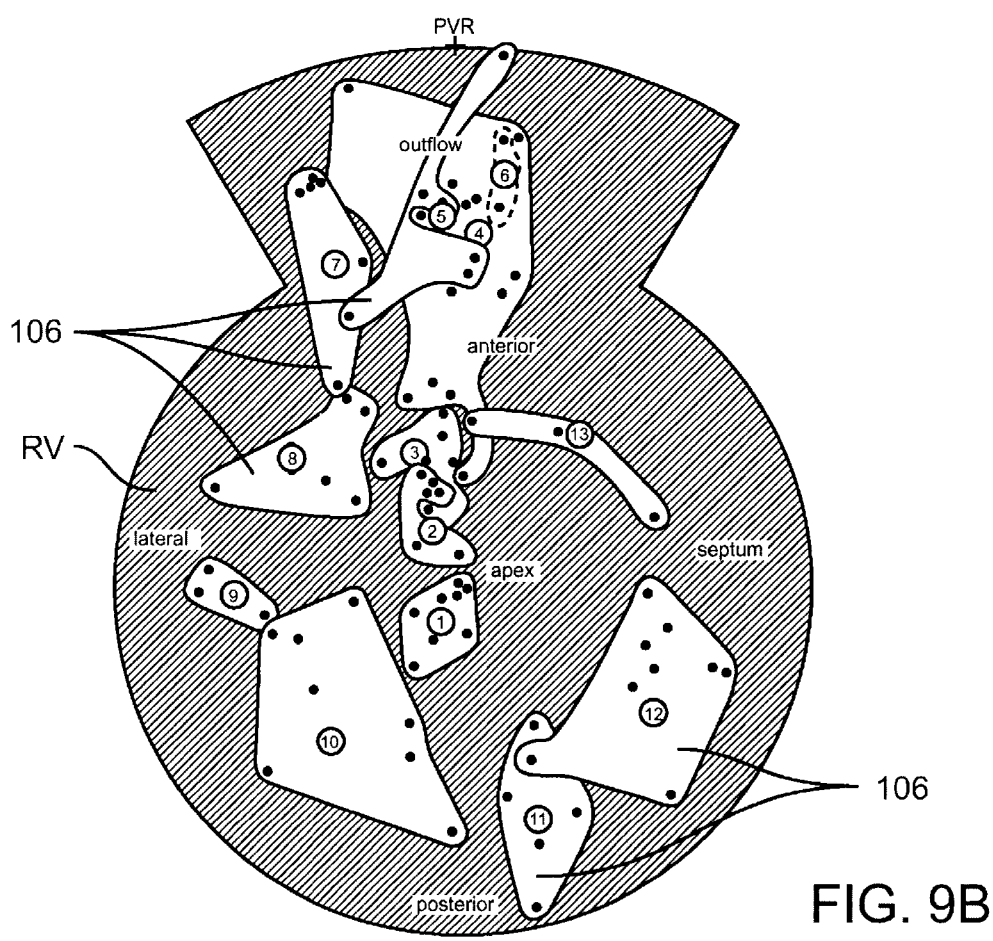

In known localization methods, a mean paced integral plot from the database is often selected as the closest correlation to the arrhythmia integral plot for a particular patient. An arrhythmogenic region associated with the corresponding mean paced plot as effectively been identified. Arrhythmogenic regions 106 associated with mean paced plots 1–25 of left ventricular database 84 (shown in FIG. 8) and plots 1–13 of right ventricle database 82 (shown in FIG. 7) are illustrated in FIGS. 9A and 9B, respectively. In many embodiments, these arrhythmogenic regions will be discrete locations based on the information within the associated database. Preferably, arrhythmogenic regions 106 will have surface areas of less than about 5 cm². Optionally, the arrhythmogenic regions may have an outer radius which is less than about 2.5 cm, ideally about 1.0 cm or less. In some embodiments, the arrhythmogenic regions identified by sensor array 10 on the patient's torso (shown in FIG. 1A) may be small enough that no further localization is needed, and ablation of the ectopic site within the arrhythmogenic region may proceed without excessive collateral damage.

A limitation of known methods for using a database of pacing locations and associated heart signals is that they generally rely on database look-up methodology. Such methods provide discrete results in that the localization result is selected as one out of a limited set of possible origin segments (often being about 25 or less discrete possible segments). Removing the discreteness that database look-up methods impose and instead providing continuous estimates of candidate ectopic or exit sites using the full information content of a database should provide significant advantages in resolution and localization accuracy. Perhaps even more importantly, if two or more paced integral maps are obtained from the same patient in a single session, an even more precise estimate of the ectopic origin or exit site relative to the pacing sites can be provided to guide subsequent positioning of the catheter. In general, the description below will refer to the use of QRS Integral maps (QRSI's) for localization of an exit site for VT. As mentioned above, similar methods may find use for localization of a variety of ectopic origins or exit sites for many arrhythmias.

Paced QRSI patterns originating from the left ventricle may be primarily determined by the corresponding position on the endocardial surface of the left ventricular wall. By assuming that the activation sequence is uniquely determined by the pacing site (without excessive patient-to-patient variations), and by assuming that the QRSI varies continuously within the endocardial position of the origin, then there exists a surface S in an N-dimensional QRSI (N here being the number of sensor locations or interpolated sensor data, for example, 192 locations), with each point corresponding to an endocardial position. By identifying S, we can compute the position in a two-dimensional approximation of the endocardium from a given QRSI by projecting it on S, and applying a $R^2 \rightarrow R^2$ function.

The amplitude of a QRSI may not contain information on the site of origin so that we can assume that S is star-convex with respect to the origin of map space, and project it on a unit sphere in the first three-dimensions after application of a Karhunen-Loeve (KL) transform, previously determined from a large set of paced QRSI's. S can then be parameterized using spherical coordinates. The translation to the endocardial surface is obtained by fitting a continuous mapping function to a set of paced maps and their measured pacing positions.

Figures 10A, 10B:
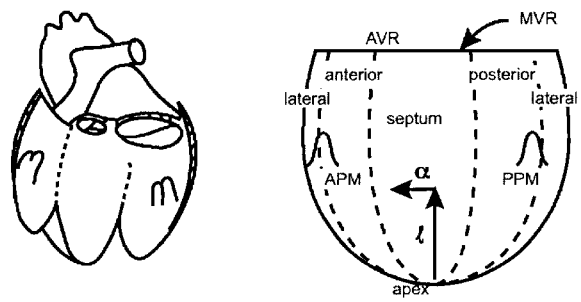
FIGS. 10A–C illustrate alternative views of the left ventricle with FIG. 10C showing pacing sites and pacing segments associated with 25 mean paced maps for the left ventricle in cylindrical coordinates having an axis extending between a center of the mitral valve ring and the apex of the left ventricle.
Figure 10C:
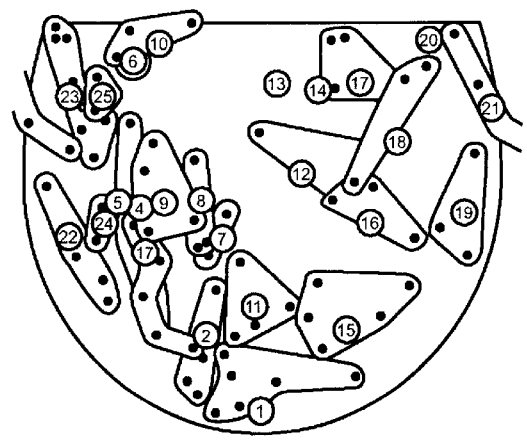

Referring now to FIGS. 10A–C, the endocardial wall may be described using left ventricular cylindrical coordinates. These coordinates are based on the line from the geometric middle of the mitral valve ring to the apex. The ventricular length l is the axial position from the apex normalized to the axis length; the ventricular angle α is the angle of a position relative to the angle of the aortic valve ring. FIG. 10B illustrates these concepts. FIG. 10B generally illustrates the endocardium of the left ventricle, opened at the lateral wall. The top edge represents the mitral valve ring MVR with the apex indicated at the bottom of the figure. The width mimics the circumference of the ventricle as a function of the ventricular length. Also indicated are the four longitudinal quadrants: anterior, septum, posterior, and lateral. The anterior and posterior papillary muscles APM and PPM, and the aortic valve ring AVR are shown as well. The diagram of FIG. 10B can be generated from endocardial cylindrical coordinates, with the horizontal position preferably being a fraction $\alpha/2\pi$ of the diagram width at the given length ($-\pi \leq \alpha \leq \pi$) where α represents the ventricular angle.

In the diagram of FIG. 10C, pacing sites are indicated as dots with pacing segments or regions (each associated with one of the mean paced maps) indicated with white patches, thereby graphically illustrating the locations of the known discrete ectopic sites or exit sites for a database of 25 mean paced maps for the left ventricle.

In this description, a QRSI is regarded as a 192-element vector, containing an element corresponding to each of 12×16 grid sensor data locations (many of which may comprise interpolated sensor data). A fixed KL transform, previously determined from the 99 QRSI→QRSI's, is applied to each QRSI. The covariance between the 192 'channels' of the maps is computed, and the eigenvectors $\psi_i$ of the covariance matrix are computed using MATLAB™ software. Then each QRSI $\vec{m}$ is expressed in terms of these (orthonormal) eigenvectors:

$$\vec{m} = \sum_{i=1}^{192} w_i \vec{\psi}_i$$

where $$w_i = \vec{m} \cdot \vec{\psi}_i$$

The first three coefficients $w_i$, which corresponds to the three $\psi_i$ with the largest eigenvalues, may about describe 90% or more (ideally about 97%) of the energy content $\vec{m}$.

The coefficients $w_1$, $w_2$, and $w_3$ of each map $\vec{m}$ may be treated as Cartesian coordinates in a three-dimensional space and expressed in spherical coordinates r, θ, and φ, while the other 189 coefficients are discarded. The axis of the spherical coordinate system can be chosen such that the database QRSI corresponding to the left ventricular apex has θ=0. r is an estimate of the total energy content of the map, and may be discarded if S is star-convex with respect to the origin of map space, as this also implies that only the pattern of the QRSI contains information about the site of origin. If correlation coefficients are used to compare maps, the total energy content is also discarded. The θ and φ coordinates can be mapped by two smooth, homogenous parametric mapping functions to an estimate of the site of origin, which we can treat as a two-dimensional quantity.

Referring again to FIG. 10B, a position on the left ventricular wall is denoted with a pair (l, α), where l stands for the ventricular length and α represents the ventricular angle. Estimated coordinates are indicated as $\hat{l}$ and $\hat{\alpha}$.

Figure 11:
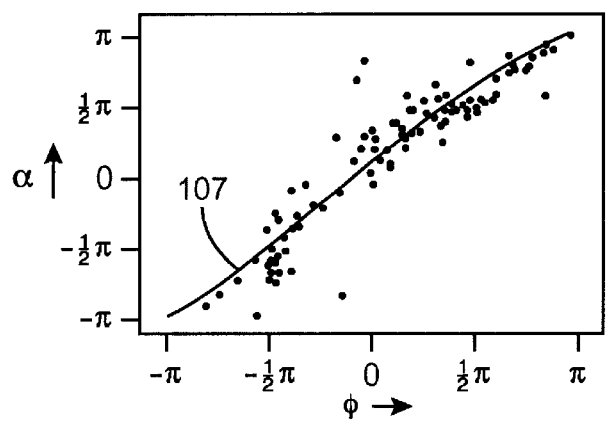
FIG. 11 illustrates measured coordinates of a database of paced maps versus a statistical mapping coordinate in a three-dimensional coordinate space correlation.
Figure 12:
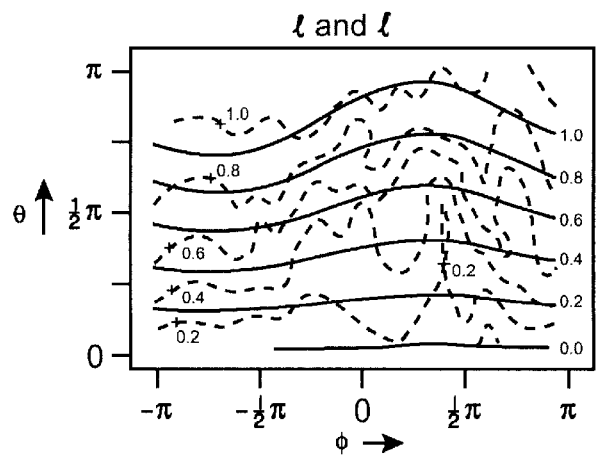
FIG. 12 illustrates measured coordinates of the paced maps interpolated in a statistical three-dimensional space with the actual and estimated axial position shown as dashed and solid lines, respectively.

The parameter of θ a QRSI corresponds approximately to the ventricular axial position l of the pacing, ectopic, or exit site, and φ corresponds approximately to the ventricular angle α. This is partly a result of definition that θ=0 in the apex. The relationship between the pairs (θ,φ) and (l, α) is illustrated in FIGS. 11 and 12. FIG. 11 illustrates the measured coordinates α of the database of 99 paced maps shown as data versus the map coordinate φ. The relation between α and φ is almost linear and can be approximated by superimposing a small sine wave on a straight line. FIG. 12 illustrates the measured coordinates l of the 99 paced maps, as interpolated in the θ-plane, shown with dashed contour lines (these contour lines being labeled with a +sign). Also shown with solid contour lines and labeled on the right side of the plot is the estimated l̂. FIG. 12 shows that l depends primarily on θ, with a small contribution of ϕ, that can be approximated by adding a sine wave contribution that is slightly larger for higher values of θ.

The following functions are devised to relate l and α to θ and ϕ:

$$\hat{\alpha} = \phi + c_1 + c_2 \sin(\phi - c_3)$$
$$\hat{l} = \theta(d_1 + d_2 \sin(\phi - d_3))/\pi$$

The parameters $c_1$ and $d_1$ of these functions are obtained by fitting the functions to the database maps. The resulting functions α̂ and l̂ are shown by solid lines in FIGS. 11 and 12, respectively.

As noted above, estimates of the difference between two pacing sites (rather than the absolute position of a pacing site) can have significant advantages in accuracy. To identify the accuracy of absolute localization, a cross validation on the 99 paced maps can be performed using the fitting procedures with all but one of the database maps, and then calculating the localization error of the omitted map, leaving out each map in turn. The differences between the computed positions and the measured positions are illustrated in FIG. 13A. The differences between the positions of the 25 database maps of the left ventricle and the corresponding computed positions of the database QSRI's is illustrated in FIG. 13B. Each map $\vec{\hat{m}}$ is represented with the triple coefficients $(w_1, w_2, w_3)$ as $m^1 = w_1 \vec{\phi}_1 + w_2 \vec{\phi}_2 + w_3 \vec{\phi}_3$. The associated representation accuracy may be expressed as $$\sum_{i=1}^{3} w_i^2 \bigg/ \sum_{i=1}^{192} m_i^2$$

with $w_i$ as defined in the previously mentioned equation that expressed each QRSI $\vec{m}$ in terms of (orthonormal) eigenvectors. For the 99 pace maps, this number was 97±2% (range 90–99%).

The distance between the measured and computed position of the 99 pace maps is 14.6±8.2 mm; the distance between the 25 segment positions and the segment positions computed from the corresponding mean paced maps is 9.2±3.0 mm.

Referring now to FIG. 14, when pairs of paced maps are considered from the same patient with pacing locations which are near to each other, the relative localization error can also be estimated. Computed and measured positions corresponding to eight paced maps obtained at similar locations (the middle and basal posterior wall of the left ventricle) in a single patient are illustrated in FIG. 14. Although significant positional errors are indicated, they are closely related and the relative positions of measured and computed locations (i.e., an adjustment vector) are roughly the same.

As illustrated in FIG. 15, the localization error decreases significantly as the number of maps increases from a single pair. This figure shows localization results obtained using produced sets of maps for the fitting procedure, and using the remaining maps for testing. FIG. 15 also shows that the mean error is roughly constant from about 98 maps to about 20 maps with the maximum error increasing only slightly when the number of maps is reduced below about 40. The mean error is shown with a solid line, while the minimum and maximum errors are shown with dashed lines.

In general, localization using the techniques of the general invention will benefit significantly from a database which includes both accurate integral maps and accurate location information of the pacing location, ectopic origin, exit site, or the like. Magnetic localization using ultra low magnetic fields and a special catheter containing a miniature magnetic field sensor, or electrical localization using catheter electrodes which measure the local potential induced by small currents supplied at the body surface may have significant advantages for accurate identification of pacing sites. Ultrasound based determination of the three-dimensional catheter position such as that used in the Real-Time Position Management System™ now being commercialized by CARDIAC PATHWAYS CORPORATION. may also be suitable for use to identify actual locations. Location information provided by a Charge Coupled Device (CCD) coupled to an image analyzer and based on biplane fluoroscopy may also be of use. Suitable location identification systems and components are commercially available from a variety of sources. For example, three-dimensional magnetic localization systems having device location display capabilities are available from BIOSENSE WEBSTER, while electrical localization systems may be commercially available from MEDTRONIC, INC., under the tradename LOCALISA™. These and other systems may be suitable for use with the present invention, such systems ideally being modified to take advantage of the calculations described herein and/or to provide catheter navigation information to the physician. The navigation information may comprise a graphical catheter movement guide, the guide optionally being superimposed with an image of the heart tissue (ideally in three-dimensional, such as on two orthogonal biplane fluoroscopic images or the like). The guide may comprise a position adjustment vector (optionally in polar format, three-dimensional anatomical format, or both), and/or a target catheter position marker.

Application of these continuous localization techniques, both absolute and relative, for diagnosis and/or treatment of cardiac arrhythmias may, in some cases, benefit from consideration of additional indicators to differentiate locations having nearly similar integral plots. Although localization may be possible in many circumstances with reference solely to integral map shapes, the absolute amplitude of the integral may help differentiate, for example, ectopic or exit sites located along the septum of the right ventricle from ectopic or exit sites located along the lateral wall of the right ventricle.

Figure 16:
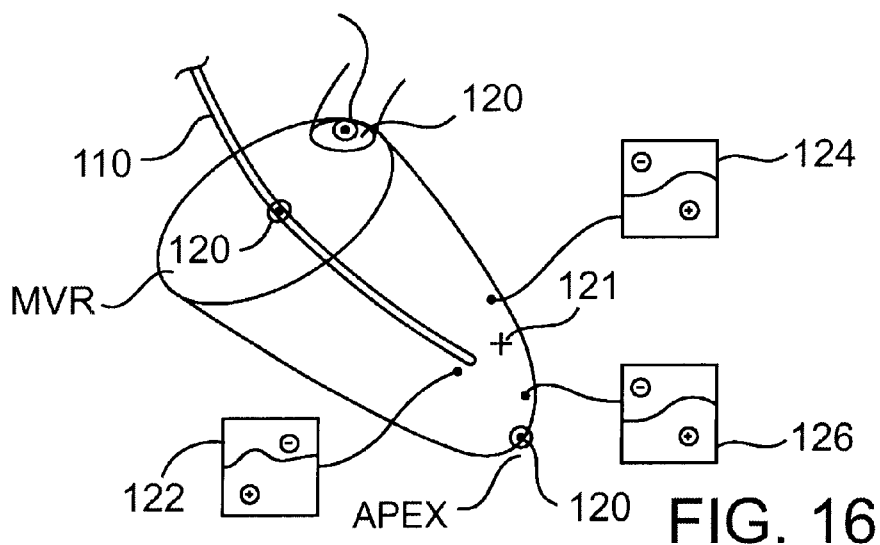
FIGS. 16 and 17 schematically illustrate a method for locating a position and orientation of a chamber of a heart in space, and also schematically illustrate relative localization using information obtained from a particular patient.
Figure 17:
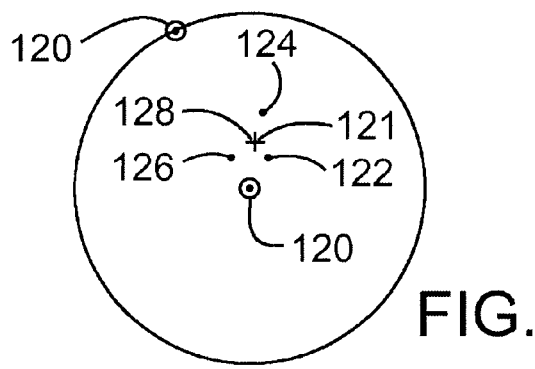

Referring now to FIG. 16, and as was described above with reference to FIG. 2, it will often be beneficial to identify a location and orientation of the endocardial surface of a chamber of the heart, particularly when a system is intended to guide a catheter toward a candidate site. Additionally, size information regarding the chamber may be used to apply normalized data to the specific patient. Advantageously, pacing and/or ablation catheter 110 may be used to identify datum locations 120 so as to indicate to the system the general layout of the heart chamber. For example, by identifying a center or perimeter of a mitral valve ring MVR, an apex, and a center of an aortic valve ring AVR, often by sequentially positioning catheter 110 at these tissue structures and taking catheter location measurements at each location, the basic geometry of the patient's heart chamber can be readily modeled by the system. Related calculations are described in more detail in a draft article entitled, "*Conversions From Left Ventricular Cylinder Coordinates To Radiographic Projections During ECG-Guided Catheter Ablation of Cardiac Arrhythmias*," attached as Appendix A hereto and incorporated herein by reference.

Referring to FIGS. 16–18B, based on a calculated candidate site and the chamber geometry, the system may generate one or mores sequential graphical position indications 121 to help guide the physician during positioning of catheter 110. The graphical candidate site indicator (or guide) 121 will be revised after each sequential paced map 122, 124, 126 is obtained. Initially, the information included in each paced map may be used in combination with a general database (although even initially it may be used independent of any external database). As more and more patient-specific information is obtained, guide marker 121 should more and more accurately approximate the actual ectopic or exit site. Once sufficient patient/specific information has been obtained, that information may optionally be used independent of any database (if a general database was initially used).

Figure 18A:
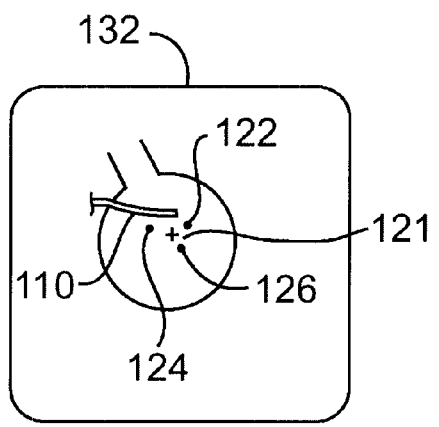
FIGS. 18A and 18B schematically illustrate biplane three dimensional guided positioning of a catheter for diagnosis and/or treatment of an arrhythmia.
Figure 18B:
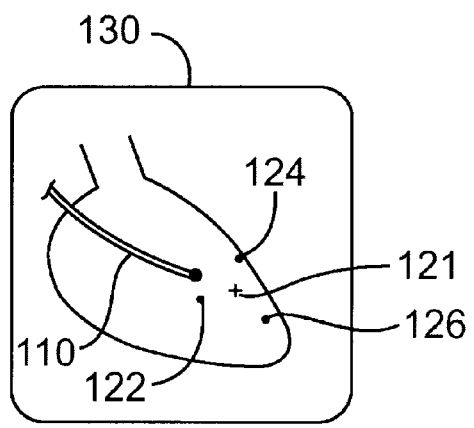

Preferably, guide 121 will provide a three-dimensional position indication, such as by providing separate markers on a right anterior oblique angled fluoroscopic display 130 illustrated in FIG. 18B, and on a left anterior oblique angled display 132 illustrated in FIG. 18A. A variety of other projections and imaging modalities can also be used. Such a three-dimensional guide is particularly advantageous when superimposed on an image of the heart tissue and the catheter 110, as it allows the attending physician to position the catheter with reference to the tissue image and guide.

Figure 19:
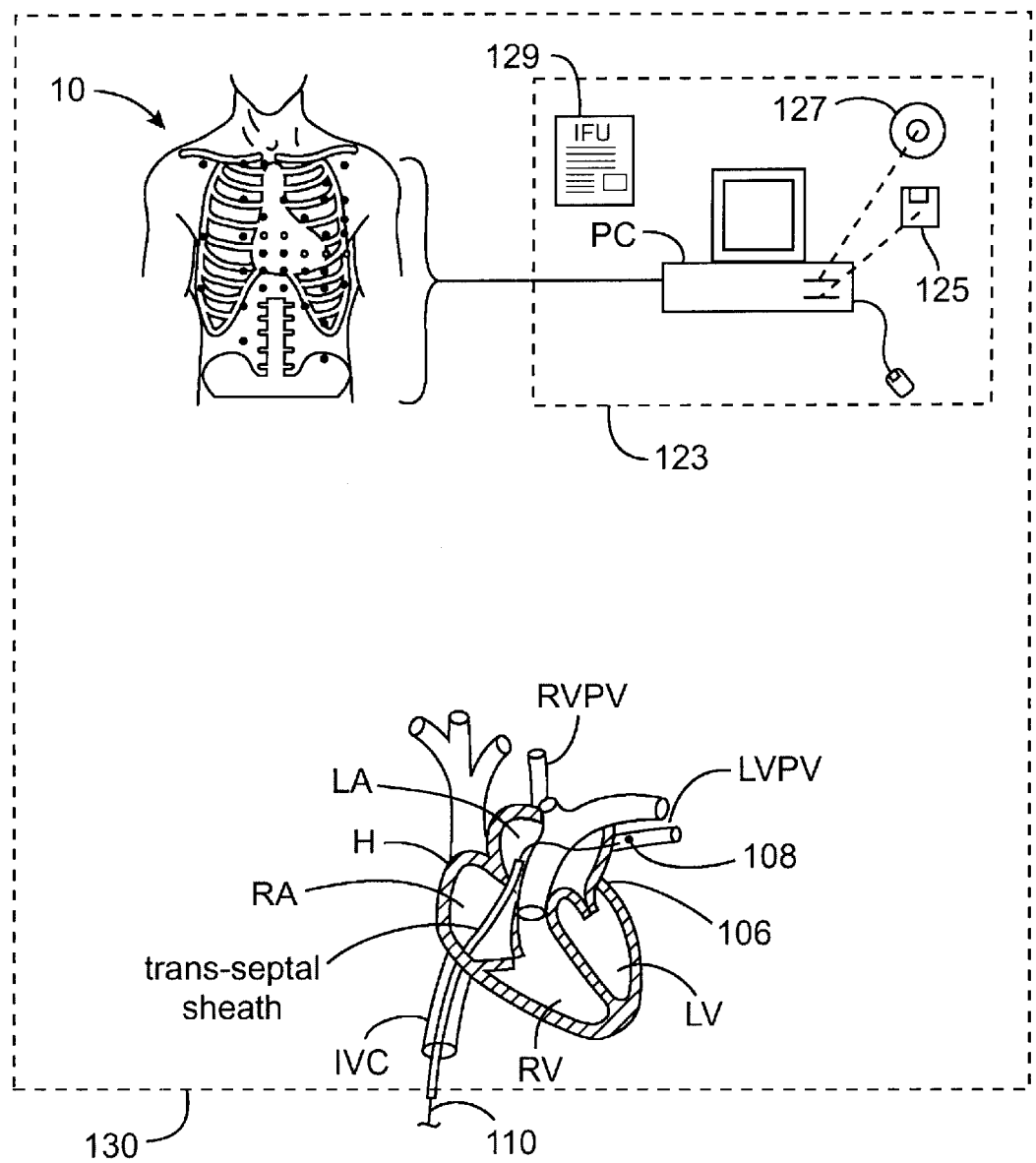
FIG. 19 schematically illustrates a system and/or kit for diagnosing and/or treating focal atrial fibrillation and other arrhythmias, according to the principles of the present invention.
Figures 20A, 20B:
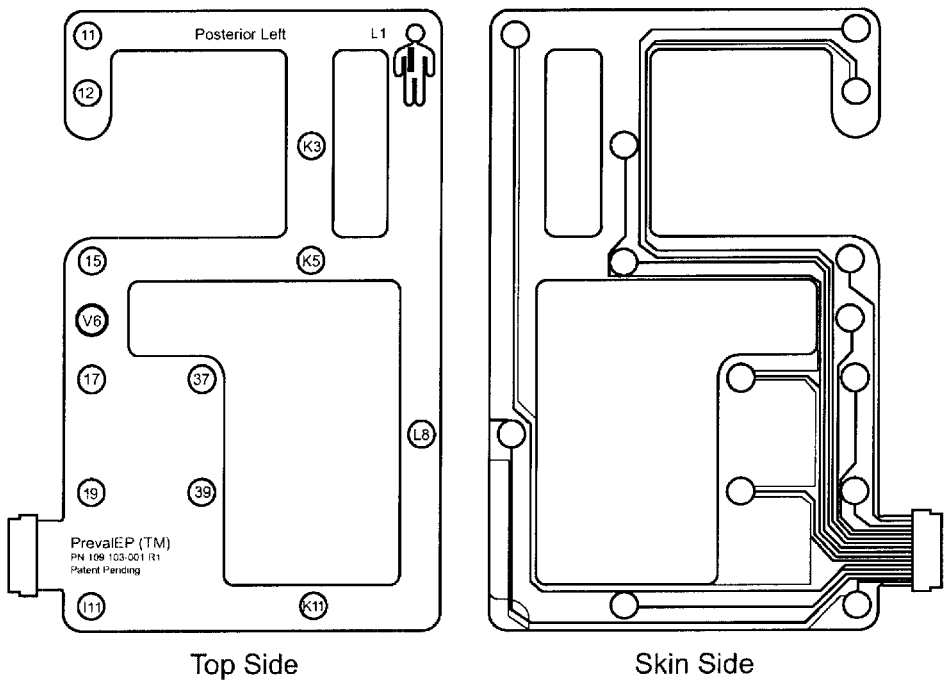
FIGS. 20A–H illustrate exposed and skin-engaging surfaces of four panels supporting heart cycle sensors in an exemplary sensor array structure.
Figures 20C, 20D:
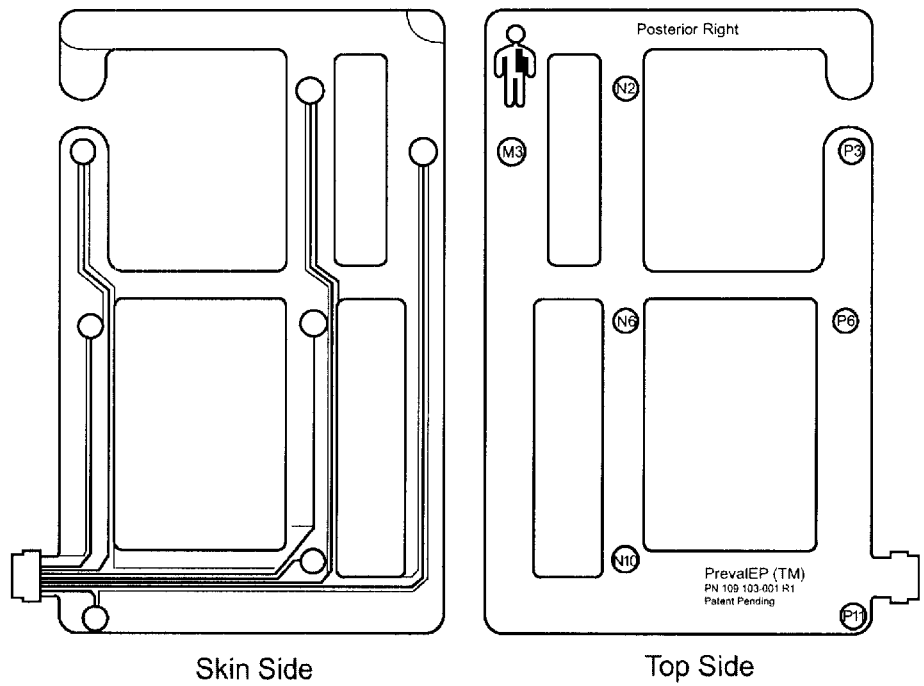
Figure 20E:
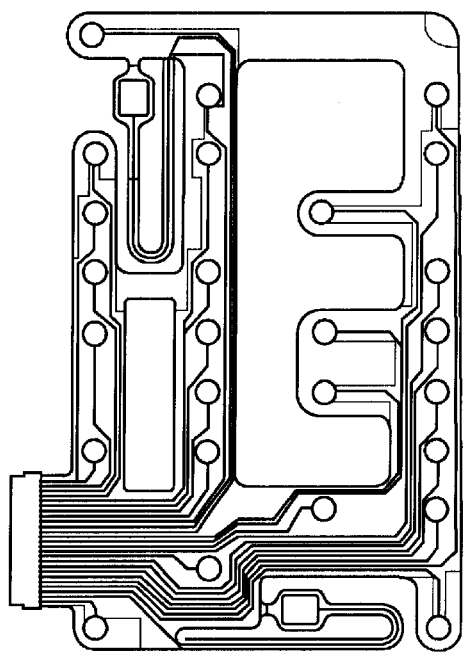
Figure 20F:
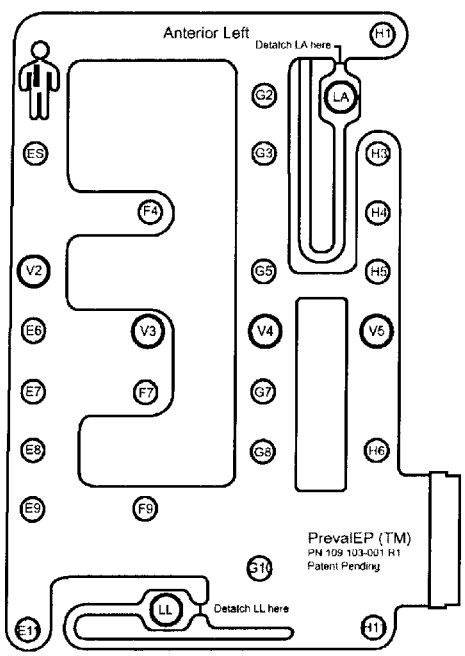
Figure 20G:
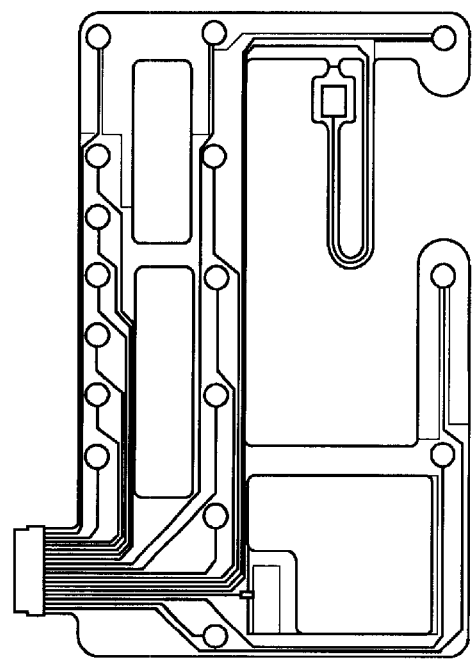
Figure 20H:
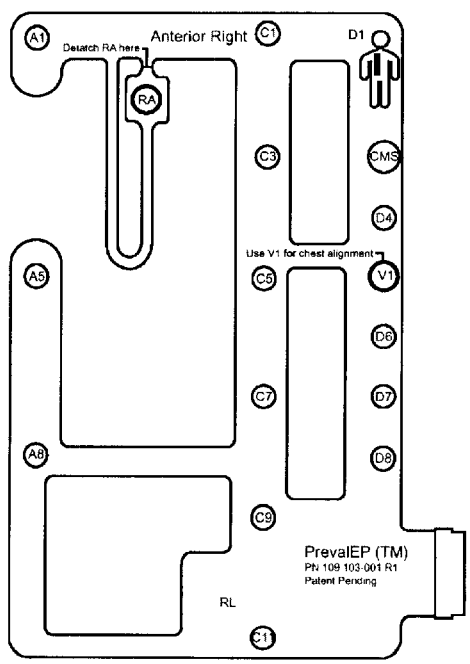

Referring now to FIG. 19, once an ectopic origin 108 within arrhythmogenic region 106 has been sufficiently localized, ablation of the ectopic origin 108 is effected, often using an ablation electrode of pacing catheter 110. A variety of alternative tissue treatment modalities might be applied to the ectopic origin, including radio-frequency ablation, cryogenic cooling, ultrasound, laser, microwave, bioactive agents, and the like. Similarly, a variety of intracardiac localization techniques might be used in place of intracardiac pace mapping under fluoroscopy. Suitable three-dimensional electro-anatomical point-by-point mapping systems may be commercially available for localization of an ectopic origin within an arrhythmogenic region from BIOSENSE-WEBSTER, INC. under the trademark CARTO®, and a related Real-Time Position Management™ system may be available from CARDIAC PATHWAYS CORPORATION. Alternative multi-electrode catheters may be commercially available from CARDIMA, INC., BIOSENSE-WEBSTER, INC., CARDIAC PATHWAYS CORPORATION, BARD, INC. and/or EP TECHNOLOGIES, INC. A still further alternative for localizing of the ectopic origin within an arrhythmogenic region may be provided using a three-dimensional non-contact multi-electrode mapping system available from ENDOCARDIAL SOLUTIONS, INC. Exemplary cryogenic systems may be available from CRYOCATH, INC. and from CRYOGEN, INC. A suitable cooled radiofrequency ablation catheter is sold commercially as the CHILLI®-Cooled Ablation System from CARDIAC PATHWAYS CORPORATION. Pulmonary vein isolation systems for use with the invention are now being developed by ATRIONIX (ultrasound) and CARDIOFOCUS (laser ablation).

Referring to FIG. 19, a kit 123 for localization of an arrhythmogenic region of heart H may include a tangible media having a machine-readable code embodying any of the methods described herein above. Media 125 will often be used in a general-purpose computer PC coupleable to array 10, with the PC typically having a processor for effecting the method steps embodied in media 125, as well as input devices such as a mouse, keyboard, an Internet, Ethernet, and/or Intranet, as well as output devices such as monitor, a printer, an I/O port, and/or the like. The PC will often manipulate the data in response to heart cycle signals sensed by array 10, and also in response to a heart cycle signal database 127, as described herein above. Instructions for use 129 will often be included within kit 123, with the instructions and at least one other component of the kit often being packaged together, instructions for use 129 optionally being embodied as printed information (optionally appearing at least in part on the packing material), a VCR tape, media embodying a machine readable code, or the like.

In many embodiments a system 130 will include one or more components of kit 123, and may also include array 10 and/or a probe such as catheter 110 for localization and/or treatment of the arrhythmias.

Yet another exemplary set of four panels is shown in FIGS. 20A–H. Both the radially exposed outer surfaces of the panels and the skin engaging surfaces are illustrated, and the indicia of panel positioning (herein the form of a graphical highlight on a human figure) and other structures described above are clearly seen.

While the exemplary embodiments have been described in some detail, by way of example and for clarity of understanding, a variety of changes, adaptations, and modifications will be obvious to those of skill in the art. Hence, the scope of the present invention is limited solely by the appended claims.

What is claimed is:

1. An arrhythmia localization method making use of a database, the database including known heart signals and associated discrete known ectopic or exit sites, the arrhythmia localization method comprising:
   measuring heart signals during an arrhythmia; and
   identifying a candidate ectopic or exit site which is different than the known sites by comparing the measured heart signals to a plurality of known heart signals.

2. The arrhythmia localization method of claim 1, further comprising sensing the heart signals with an array of sensors distributed across an accessible body surface.

3. The arrhythmia localization method of claim 2, wherein the array has at least 6 sensing locations distributed across a torso.

4. The arrhythmia localization method of claim 3, further comprising integrating a selected portion of the measured heart signals at each sensing location to determine an associated integral value and generating a data matrix by arranging the integral values according to the associated sensing locations, the comparing step comprising comparing the data matrix with data matrices of the database generated from the known heart signals.

5. The arrhythmia localization method of claim 4, further comprising interpolating between a plurality of the known sites associated with the plurality of known heart signals based on the comparison of the measured heart signals to a plurality of the known heart signals.

6. The arrhythmia localization method of claim 5, further comprising determining correlations between the known heart signals and known sites, and selecting the candidate site using a statistical comparison of the measured heart signals with the known heart signals.

7. The arrhythmia localization method of claim 1, further comprising normalizing the database by transforming the known sites into a uniform coordinate system.

8. The arrhythmia localization method of claim 7, wherein the uniform coordinate system comprises a member selected from the group consisting of polar coordinates and cylindrical coordinates having an axis extending from an apex to a mitral or tricuspid valve ring and normalized based on a distance therebetween.

9. The arrhythmia localization method of claim 1, further comprising measuring paced heart signals by generating an artificial arrhythmia at a pacing site, wherein the candidate site identification is based in part on the paced signals.

10. The arrhythmia localization method of claim 9, wherein the candidate site is determined by calculating an estimated ectopic or exit site with the measured heart signal and the known heart signals, by calculating an estimated pacing site from the paced heart signals and the known heart signals, and by modifying the estimated site to generate the candidate site based on a difference between estimated pacing site and the pacing site.

11. The arrhythmia localization method of claim 9, further comprising generating a plurality of arrhythmias at a plurality of pacing sites, wherein the candidate site identification is based in part on the plurality of pacing sites.

12. The arrhythmia localization method of claim 1, further comprising measuring paced heart signals by generating a plurality of artificial arrhythmias at a plurality of pacing sites of a patient to generate the database, and wherein the measured heart signal is measured from said patient.

13. The arrhythmia localization method of claim 1, further comprising imaging a heart tissue and graphically indicating the candidate site on an image of the heart tissue.

14. The arrhythmia localization method of claim 13, wherein the image of the heart tissue comprises a three-dimensional image, and wherein the candidate site is indicated as a three-dimensional position.

15. The arrhythmia localization method of claim 14, further comprising positioning a catheter at the candidate site by reference to the graphical indication.

16. An arrhythmia localization system comprising:
   a database having known heart signals and associated discrete known ectopic or exit sites;
   a heart signal sensor array for measuring heart signals during an arrhythmia; and
   a processor coupled to the database and the sensor array, the processor calculating a candidate ectopic or exit site, which is different than the known sites, in response to the measured heart signals and the known heart signals.

17. The arrhythmia localization system of claim 16, wherein the sensor is adapted for engaging a torso to define at least 6 sensing locations distributed across at least two dimensions of the torso.

18. The arrhythmia localization system of claim 17, wherein the processor integrates a selected portion of the measured heart signals at each sensing location to determine an associated integral value and generates a data matrix of the integral values according to the associated sensing locations, the processor comparing the data matrix with data matrices of the database generated from the known heart signals.

19. The arrhythmia localization system of claim 18, wherein the processor interpolates between a plurality of the known sites associated with the plurality of known heart signals based on the comparison of the measured heart signals to a plurality of the known heart signals.

20. The arrhythmia localization system of claim 19, the processor determining correlations between the known heart signals and known sites, and selecting the candidate site using a statistical comparison of the measured signals with the known signals.

21. The arrhythmia localization system of claim 16, wherein the processor normalizes the database by transforming the known ectopic or exit sites into a uniform coordinate system.

22. The arrhythmia localization system of claim 21, wherein the uniform coordinate system comprises a member selected from the group consisting of polar coordinates and cylindrical coordinates having an axis extending from an apex to a mitral or tricuspid valve ring and normalized based on a distance therebetween.

23. The arrhythmia localization system of claim 16, wherein the sensor array transmits paced heart signals to the processor, the paced heart signals resulting from an artificial arrhythmia generated at a pacing site, wherein the candidate site identification is calculated with the paced signals.

24. The arrhythmia localization system of claim 23, wherein the candidate site is determined by calculating an estimated ectopic or exit site with the measured heart signal and the known heart signals, by calculating an estimated pacing site from the paced heart signals and the known heart signals, and by modifying the estimated site based on a difference between the estimated pacing site and the pacing site.

25. The arrhythmia localization system of claim 23, wherein the candidate site is calculated in response to a plurality of pacing sites.

26. The arrhythmia localization system of claim 16, the database comprising a plurality of heart signals induced by pacing at a plurality of pacing sites of a patient, and wherein the candidate site identifies a location of a heart tissue of said patient.

27. The arrhythmia localization system of claim 16, further comprising an imaging system coupled to the processor, the imaging system graphically indicating the candidate site on an image of the heart tissue.

28. The arrhythmia localization system of claim 27, wherein the image of the heart tissue comprises a three-dimensional image, and wherein the candidate site is indicated as a three-dimensional position.

29. The arrhythmia localization system of claim 27, further comprising a catheter having a distal portion with an image visible with the imaging system, the catheter having at least one of an arrhythmia treatment element and a pacing element.

30. The arrhythmia localization system of claim 29, further comprising a catheter localization system coupled to the processor for transmitting catheter element location signals.

31. The arrhythmia localization system of claim 16, further comprising a display coupled to the processor, the display showing navigation information for positioning of a probe in alignment with the candidate site for treatment of the arrhythmia.

32. The arrhythmia localization system of claim 31, wherein the navigation information comprises a candidate site marker or a vector indicating a desired probe movement from an actual position to the candidate site.

33. The arrhythmia localization system of claim 16, wherein the processor generates a potential map indicating potential distribution across the array at a sensing time.

* * * * *